US011386986B2

(12) United States Patent
Thomas et al.

(10) Patent No.: US 11,386,986 B2
(45) Date of Patent: Jul. 12, 2022

(54) SYSTEM AND METHOD FOR IDENTIFYING COMPLEX PATIENTS, FORECASTING OUTCOMES AND PLANNING FOR POST DISCHARGE CARE

(71) Applicant: GE Precision Healthcare LLC, Milwaukee, WI (US)

(72) Inventors: Bex George Thomas, Laguna Nigel, CA (US); Andrew Day, Newton, PA (US); Savanoor Pradeep Rai, Naperville, IL (US); Ryan Mancl, Austin, TX (US); Hong Yang, Hoffman Estates, IL (US); Rulin Chen, Chicago, IL (US); Leonardo Dias, Toronto (CA)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 171 days.

(21) Appl. No.: 16/588,250

(22) Filed: Sep. 30, 2019

(65) Prior Publication Data
US 2021/0098090 A1 Apr. 1, 2021

(51) Int. Cl.
*G16H 10/60* (2018.01)
*G16H 40/20* (2018.01)
(Continued)

(52) U.S. Cl.
CPC ............. *G16H 10/60* (2018.01); *G06N 20/00* (2019.01); *G16H 20/00* (2018.01); *G16H 40/20* (2018.01); *G16H 50/30* (2018.01)

(58) Field of Classification Search
CPC ........ G16H 10/60; G16H 20/00; G16H 40/20; G16H 50/30; G16H 50/50; G16H 50/20;
(Continued)

(56) References Cited

U.S. PATENT DOCUMENTS 10,679,746 B1 * 6/2020 Fletcher ................. G16H 40/63
2012/0296671 A1 * 11/2012 Simons-Nikolova .......................
G16H 50/30
705/2

(Continued)

*Primary Examiner* — Fonya M Long
*Assistant Examiner* — Alaaeldin M Elshaer
(74) *Attorney, Agent, or Firm* — Amin, Turocy & Watson, LLP

(57) ABSTRACT

Techniques are described for identifying complex patients and forecasting patient outcomes based on a variety of factors including medical, socio-economic, mental and behavioral. According to an embodiment, a method can include employing one or more machine learning models to identify complex patients and predict patient outcomes like length of stay, potential discharge trajectories with likelihoods, discharge destinations, readmission likelihood and safety. These models are applied to respective patients that are currently admitted to a hospital and expected to be placed after discharge from the hospital, wherein the one or more discharge forecasting machine learning models predict the discharge destinations based on clinical data points and non-clinical data points collected for the respective patients. The method can further include providing discharge information identifying the discharge destinations predicted for the respective patients to one or more care providers to facilitate managing and coordinating inpatient and post-discharge care for the respective patients.

29 Claims, 18 Drawing Sheets

(51) Int. Cl.
  *G16H 50/30* (2018.01)
  *G16H 20/00* (2018.01)
  *G06N 20/00* (2019.01)
(58) Field of Classification Search
  CPC ........ G16H 50/70; G06N 20/00; G06Q 50/22; G06Q 10/02
  USPC ........................................................ 705/2, 3
  See application file for complete search history.

(56) References Cited

U.S. PATENT DOCUMENTS

| | | | |
|---|---|---|---|
| 2015/0363568 A1* | 12/2015 | Milo | G16H 50/30 705/2 |
| 2017/0061093 A1* | 3/2017 | Amarasingham | G16H 40/63 |
| 2019/0034590 A1 | 1/2019 | Oren et al. | |
| 2020/0258617 A1* | 8/2020 | Hayashitani | G16H 50/20 |
| 2020/0365255 A1* | 11/2020 | Hayashitani | G16H 50/20 |

* cited by examiner

DISCHARGE BARRIERS — 1200

| PATIENT | | TASKS | DISCHARGE | |
|---|---|---|---|---|
| L.MCA MRN1652<br>CARD TJUH 7135A<br>INS. AAN | ADM 2/25<br>LOS 8<br>EDD 3/5 | 🚗 | STATUS CONFIRMED<br>TRANS DATE<br>TRANS TIME | |
| P.LIG MRN1259<br>MED TJUH 7135A<br>INS. MVP | ADM 2/26<br>LOS 7<br>EDD 3/5 | 🏥 | STATUS CONFIRMED<br>TRANS DATE 3/5<br>TRANS TIME 3:45PM | |
| M.JOS MRN12412<br>MED TJUH 1049<br>INS. MVP | ADM 2/28<br>LOS 5<br>EDD 3/5 | 🚗 | STATUS POSSIBLE<br>TRANS DATE<br>TRANS TIME | |

SYSTEM AND METHOD FOR IDENTIFYING COMPLEX PATIENTS, FORECASTING OUTCOMES AND PLANNING FOR POST DISCHARGE CARE

TECHNICAL FIELD

This application relates to computer-implemented techniques for forecasting patient discharge events and needs using machine learning analytics.

BACKGROUND

Care providers face multiple challenges in identifying complex patients, managing care plans and forecasting patient outcomes to plan post discharge care. Discharge planning for complex patients is a process that seeks to safely transfer patients and prevent future readmissions by ensuring they receive the proper continuity of care after leaving the hospital. Inpatient discharge planning for complex patients is a critical decision point in patient care, with implications for the intake capacity of the inpatient unit as well as other units of the hospital. Effective discharge planning informed by the prospective outcomes of complex patients can ensure a patient's continued care needs are met, decrease the chances of readmission, aid recovery, ensure medications are prescribed and given correctly, and adequately prepare the patient and the patient's family for the next phase of the patient's care. Early planning and coordination by the healthcare team, including physicians, social workers, rehabilitation specialists, and post-acute care services, improves inpatient care quality and access while reducing costs. Care providers need help identifying complex patients, learning more about their prospective outcomes and planning their care both before and after their discharge.

SUMMARY

The following presents a summary to provide a basic understanding of one or more embodiments of the invention. This summary is not intended to identify key or critical elements or delineate any scope of the different embodiments or any scope of the claims. Its sole purpose is to present concepts in a simplified form as a prelude to the more detailed description that is presented later. In one or more embodiments described herein, systems, computer-implemented methods, apparatus and/or computer program products are described that provide for forecasting patient discharge events and needs using machine learning analytics to facilitate managing and coordinating inpatient and post-discharge care. In this regard, techniques are described for forecasting patient outcomes, including discharge destination placement and likelihood, length of stay (LOS), readmission risk, and safety risk, based on a variety of factors including medical, socio-economic, mental and behavioral factors, using machine learning analytics. Techniques are also described for identifying complex patients based on these of factors using machine learning, qualitative and hybrid methods.

According to an embodiment, a system is provided that comprises a memory that stores computer executable components, and a processor that executes the computer executable components stored in the memory. The computer executable components can comprise a complex patient identification component that employs machine learning, qualitative and hybrid methods to identify complex patients included amongst patients currently admitted to a hospital based on a variety of patient information about the patients, including information regarding medical complexity, socio-economic conditions, insurance, medications, behavioral factors and mental health factors. The computer executable component can further comprise a forecasting component that employs one or more forecasting machine learning models to predict care outcomes for the complex patients based on the patient information, including remaining LOS in the hospital, discharge destinations and their likelihoods, readmission risks and safety risks. The computer executable components further comprise a reporting component that provides patient care outcomes information to one or more care providers to facilitate managing and coordinating inpatient and post-discharge care for the respective patients, wherein patient care outcomes information identifies the complex patients, their length of stay, their discharge destinations and likelihoods, their readmission risks, and their safety risks. For example, in some implementations, the computer executable components can comprise a display component that displays the patient care outcomes information in real-time at one or more devices associated with the one or more care providers.

According to another embodiment, a system is provided that comprises a memory that stores computer executable components, and a processor that executes the computer executable components stored in the memory. The computer executable components can comprise a discharge destination forecasting component that employs one or more discharge forecasting machine learning models to predict discharge destinations where respective patients that are currently admitted to a hospital will be placed after discharge from the hospital, wherein the one or more discharge forecasting machine learning models predict the discharge destinations based on clinical data points and non-clinical data points collected for the respective patients. The computer executable component can also comprise a reporting component that provides discharge information identifying the discharge destinations predicted for the respective patients to one or more care providers to facilitate managing and coordinating inpatient and post-discharge care for the respective patients. In some implementations, the discharge destination forecasting component further employs the one or more discharge forecasting machine learning models to determine probabilities that the respective patients will be placed at the discharge destinations, and the reporting component includes the probabilities in the discharge information.

In some implementations, the non-clinical data points comprise information regarding post-discharge patient support, including individuals responsible for caring for the respective patients after their discharge from the hospital, such as friends, family members, home care assistants, and the like. The non-clinical data points can also comprise information regarding patient socioeconomic status (e.g., income level, standard of living, tax bracket, profession, etc.). The non-clinical data points can also comprise patient demographic information (e.g., age, gender, ethnicity, home location, religion, marital status, etc.), and patient insurance information. The clinical data points can include both historical medical information about a patient received from one or more existing databases (e.g., electronic health record (EHR) databases) as well as clinical data collected for a patient from various data sources in real-time over the course of their inpatient stay. For example, the clinical data points can include tracked vital signs, tracked clinical events, tracked patient status and location information, scheduled procedures, and the like. The clinical data can also include information regarding laboratory studies and imaging studies performed, including timing of performance, type of study performed, results, and the like. The clinical data can also include case worker information reported by case workers assigned to the respective patients.

In various implementations, the one or more discharge forecasting machine learning models include different models respectively configured to predict possible discharge destinations where the respective patients will be placed after discharge from the hospital based on different subsets of the clinical data points and the non-clinical data points, or based on different weighting schemes used for the clinical points and the non-clinical data points. With these embodiments, the discharge destination forecasting component can further employs an optimization component to facilitate determining the discharge destinations based on the possible discharge destinations, defined discharge constraints, and defined discharge optimization criteria. The computer executable components can further comprise a feedback component that receives feedback information regarding patient needs and barriers associated with placing the respective patients at the discharge destinations, and a model optimization component that optimizes the one or more discharge destination forecasting machine learning models based on the user feedback.

In some implementations, the computer executable components further comprise a LOS forecasting component that employs one or more LOS forecasting machine learning models to predict discharge times when the respective patients will be discharged from the hospital based on the clinical data points and the non-clinical data points. The discharge information provided by the reporting component can further identify the discharge times predicted for the respective patients. In some implementations of these embodiments, the LOS forecasting component can employ an optimization component to facilitate determining the discharge times based on the discharge destinations predicted for the respective patients and constraints associated with placing the respective patients at the discharge destinations. In some implementations, the one or more LOS forecasting machine learning models include different models respectively configured to predict possible discharge times when the respective patients will be discharged from the hospital based on different subsets of the clinical data points and the non-clinical data points, or based on different weighting schemes used for the clinical points and the non-clinical data points. With these implementations, the LOS forecasting component can employ an optimization component to facilitate determining the discharge times based on the possible discharge times, defined discharge constraints, and defined discharge optimization criteria. In some implementations, the computer executable components further comprise a feedback component that receives feedback information regarding patient needs and barriers associated discharging the respective patients, and a model optimization component that optimizes the one or more LOS forecasting machine learning models based on the user feedback.

The computer executable components can further comprise a complex patient identification component that identifies complex patients from amongst the respective patients, and wherein the reporting component further calls out the complex patients in the discharge information. In some implementations, the complex patient identification component identifies the complex patients based in part on the discharge destinations and likelihoods respectively predicted for the complex patients. The complex patient identification component can also determine whether a patient of the respective patients is a complex patient based on one or more of the clinical data points and one or more of the non-clinical data points collected for the patient. For example, in some implementations, the complex patient identification component can employ one or more machine learning techniques to predict whether a currently admitted patient is or is likely to become a complex needs patient based on the various clinical and non-clinical data points collected for the patient at admission and/or over the course of care.

In some embodiments, elements described in the disclosed systems can be embodied in different forms such as a computer-implemented method, a computer program product, or another form.

DESCRIPTION OF THE DRAWINGS

FIG. 11 presents an example GUI that facilitates receiving user feedback regarding patient discharge barriers and milestones in accordance with one or more embodiments of the disclosed subject matter.

FIG. 12 presents an example visualization reporting identified patient discharge barriers and associated alerts in accordance with one or more embodiments of the disclosed subject matter.

DETAILED DESCRIPTION

Figure 1A:
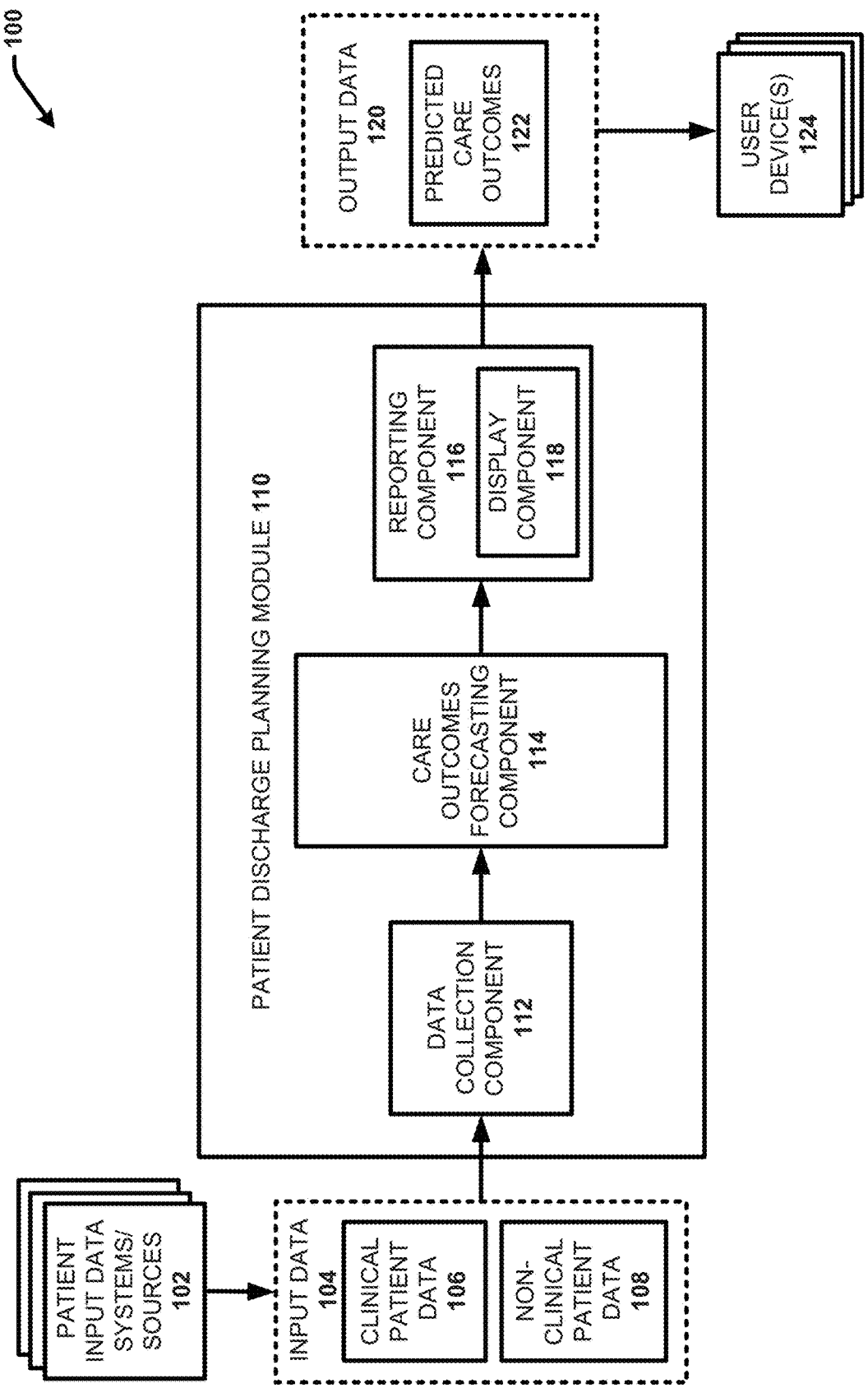
FIG. 1A illustrates a block diagram of an example, non-limiting system for forecasting patient discharge events and needs using machine learning analytics in accordance with one or more embodiments of the disclosed subject matter.

The following detailed description is merely illustrative and is not intended to limit embodiments and/or application or uses of embodiments. Furthermore, there is no intention to be bound by any expressed or implied information presented in the preceding Summary section or in the Detailed Description section.

The disclosed subject matter is directed to systems, computer-implemented methods, apparatus and/or computer program products for forecasting patient discharge events and needs using machine learning analytics to facilitate managing and coordinating inpatient and post-discharge care. Discharge planning and patient transitions are among the most complex and challenging moments in the healthcare system. At some point before the patient is discharged, the discharge disposition must be identified in order to initiate the corresponding preparation. The discharge disposition refers to the destination where a patient is being discharged. For example, a patient can be discharged home, discharged home with home professional care assistance, or discharged to a variety of post-acute care facilities, such as long-term hospitals, skilled nursing facilities (SNFs), rehabilitation facilities, and the like. The terms discharge "disposition" and discharge "destination" are used herein synonymously to indicate a type of care destination where a patient is discharged.

Hospital discharge to a post-acute setting (e.g., a non-home setting) is often among the most daunting challenges that patients and their families face. An estimated one in five hospitalized patients are discharged to post-acute care settings. There are many challenges for hospitals when planning a patient's discharge to a post-acute setting as they typically require more resources and planning than home discharges due to the increased clinical and logistical complexity of such cases. This includes insurance paperwork, coordination with any destination facilities, transportation arrangement, post discharge care planning, and patient and family instruction. Such preparation can take days, and failure to initiate in a timely manner can result in significant discharge delays. Unnecessary discharge delays not only negatively impact the patients and their families but cause increased costs to the hospital (increased costs, extra days of stay), create blockages in patient flow, increase care team and physician workload, and hinder care of potential patients not yet admitted to the hospital.

One or more embodiments of the disclosed subject matter provides systems, computer-implemented methods, apparatus and/or computer program products for predicting care outcomes of patients currently admitted to a hospital (or another type of inpatient facility) based on a variety of information collected for the patients, including medical information as well as as socioeconomic, insurance, mental health, behavioral and other types of non-clinical information. This information can be collected from various sources at various times over the course of their inpatient care. For example, a variety of clinical and non-clinical factors used to predict the patient are outcomes can be extracted from static and dynamics data sources, including patient medical records, patient admission records, insurance records, social services records, demographics records, family support information, case worker impression files, clinician reports/notes, medical monitoring devices, patient tracking systems, clinical ordering systems, procedure scheduling systems, laboratory reports, imaging study reports, and the like. In various embodiments, the care outcomes can include expected discharge destinations, expected discharge times or length of stay (LOS), expected readmission risk, forecasted safety risks and the like. The disclosed techniques can also provide for determining a probability indicating the likelihood that a patient will be discharged to a particular discharge destination, referred to herein as a "placement probability". Forecasted care outcomes (e.g., discharge destinations and associated probabilities, LOS, readmission risk, safety risk, etc.) can be regularly/dynamically updated over the course of a patient's stay to reflect changes in the patient's status and medical care needs.

The disclosed techniques for predicting patient care outcomes employ one or more machine learning models respectively trained to predict the patient care outcome based on learned correlations between a variety of unique combinations of clinical and non-clinical factors. For example, the clinical factors can include information regarding the patient's medical history prior to admission, as well as admission data regarding the reason for admission, patient status and diagnosis upon admission, initial clinical orders for the patient, an initial care plan for the patient, and the like. The clinical data can also include tracked clinical information collected for the patient over their inpatient stay, including information regarding medical procedures performed and scheduled, clinicians involved in the patient's care (e.g., physicians, nurses, technicians, etc.), laboratory tests conducted, imaging studies performed, medications administered, and the like. The tracked clinical information can also include information regarding monitored vital signs (e.g., captured and reported in real-time), monitored patient status (e.g., including changes in patient's status over time), tracked patient location, and the like.

The non-clinical factors can include various additional factors that can influence the type of post discharge care a patient will need and/or can obtain from a personal, social, logical, economic and family support perspective. For example, the non-clinical factors can include demographic factors, such patient age, gender, ethnicity, religion, language, marital status, occupation, etc. The non-clinical factors can also include factors related to the patient's socio-economic status, such as income level, net worth, credit score, standard of living, home location, assets, education level, and the like. The non-clinical factors can also include factors related to the patient's family, including information regarding whether the patient has family members that will be responsible for the patient post discharge, their respective roles in the patient's post discharge care, their respective locations, their abilities relevant to ensuring the patient's post discharge medical needs are met, and the like. The non-clinical factors can also include information regarding any other individuals (non-family members) that will be responsible for the patient post discharge and/or involved in the patient's post discharge care. In some implementations, the non-clinical factors can also include information regarding the patient's home environment, including whether the patient lives alone or with other individuals (e.g., and who these individuals are), as well as other factors that indicate whether the patient's home environment is conducive to their post discharge needs and state (e.g., structural factors, whether the home has stairs/elevators, location relative to stores, appointments, emergency services, etc.). The non-clinical factors can also include information regarding the patient's insurance provider and plan, patient preferences related to their post-discharge care, known discharge barriers, and the like. In some implementations, the non-clinical factors can also include information regarding patient behavior, patient mental health, and medication taken.

In various embodiments, the disclosed patient care outcome forecasting techniques employ and an ensemble machine learning approach that involves chaining and/or stacking of a plurality of different predictive models that respectively predict the patient care outcomes based on different combinations of clinical and/or non-clinical factors and/or using different weighting schemes for one or more of the input parameters. For example, with respect to forecasting discharge destinations and associate placement probabilities, the different predictive models can include a first model that forecasts discharge destinations based on a first set of clinical and/or non-clinical factors, a second model that forecast discharge destinations based on a second set of clinical and/or non-clinical factors, a third model that forecast discharge destinations based on a third set of clinical and/or non-clinical factors, and so on. In some implementations, the different discharge forecasting models can also include models that employ different types of machine learning algorithms/models (e.g., neural network models, decision tree models, random forest models, k-means models, etc.).

In addition to forecasting where a patient will be discharged, the disclosed systems can also employ ensemble based machine learning techniques (e.g., model stacking and chaining) to forecast when (e.g., time and date) a patient will be discharged based on the unique combinations of clinical and non-clinical data factors collected for the patient over their inpatient stay. In some implementations, the timing of discharge can be expressed as an expected length of stay (LOS). Patient care services and operations can then be aligned around this date, with the goal of minimizing delays and inefficiencies during the patient's stay, reducing their length of stay (LOS), and helping to alleviate overcrowding through improved patient flow. The forecasted discharge times can also be regularly updated over the course of their inpatient stay to reflect changes in their status, care needs, identified barriers to discharge, and other contextual factors related to their discharge (e.g., availability of beds at transition and/or discharge dispositions, coordination of transportation, etc.).

With these embodiments, the outputs of the respective models can be aggregated and evaluated using one or more optimization techniques to converge on a final discharge trajectory forecast that provides greater confidence relative to the individual models. For example, the one or more optimization techniques can determine a final discharge forecast (e.g., including one or more possible discharge destinations and associated probabilities) based on the aggregated predictions of the different models, defined discharge constraints (e.g., care needs, financial constraints, regulatory requirements, known barriers to discharge, etc.), and/or defined optimization criteria (e.g., minimize LOS, minimize discharge delay times, minimize costs, optimize patient flow, etc.). The one or more optimization techniques can also employ tailored weighting schemes for the different model outputs based on learned relevance and accuracy of the respective models for different patient groups (e.g., grouped by diagnosis, demographic factors, insurance factors, socioeconomic factors, etc.). The usage of different models respectively configured to make care outcome predictions using different sets of input parameters further enables a stacked machine learning approach, wherein different models can respectively be called and applied based on the available data for a particular patient at current point in time (e.g., when a discharge prediction is being made). In this regard, the disclosed techniques can stack and chain the appropriate models together based on the current data collected for each patient over their stay to provide predictions tailored to their individual cases and needs.

Based on predicted discharge destinations, the disclosed systems can predict well before discharge, which patients will likely require post-acute care (e.g., as opposed to home discharge), including specific types of post-acute care dispositions they will need. This allows care providers to coordinate and provide relevant care to the patients before and after hospital discharge in a timely manner. For example, patients discharged to a post-acute setting often have medically complex needs and require coordinated consultations from a variety of providers and specialists. In another example, a patient might need dialysis before and after discharge along with nursing support, or patient may need oxygen before and after discharge along with equipment support etc.

In some embodiments, patients that require post-acute care (e.g., discharge to a post-acute care destination) can be classified as complex needs patients. In one or more additional embodiments, the disclosed systems can also evaluate the various clinical and non-clinical data collected for a patient to determine or predict whether a patient is a complex needs patient and/or will be a complex needs patient upon discharge, and to determine or predict the particular care needs of the patient that make the patient a complex needs patient. With these embodiments, the disclosed systems can include a complex patient identification component that uses machine learning, qualitative and hybrid methods to identify such patients based the various clinical and non-clinical factors described herein. In this regard, identifying whether a patient needs complex care is quite different from just predicting medical events for the patient. Existing techniques for identifying complex needs patients generally involve performing risk analysis to identify patients associated with medically high risk. However, identifying complex needs patients based on medical risk alone does not provide for determining the feasible resources and the required level of care post discharge. The disclosed techniques go beyond evaluating medically complex conditions and looks at a combination of factors ranging from medical conditions, social vulnerability, mental health, behavior characteristics, insurance, medications, and other non-traditional factors, to determine whether a patient is or is likely to be a complex needs patient. Thus, the disclosed techniques provide a more accurate picture of what type of post-discharge care a complex needs patient will require and the feasible resources for providing such post-discharge care well before discharge by evaluating a variety of clinical and non-clinical factors in real-time.

In various embodiments, the disclosed systems can further provide information regarding the predicted patient care outcomes and the identified complex needs patients to care providers in real-time via a suitable rendering application to support the care delivery process. For example, in some implementations, the solution can be integrated as a visualization tile of a care delivery optimization application accessible via a network-based platform (e.g., a web-application, a website, a thin client application), a centralized command center, or another suitable operating environment. The visualization can allow a care provider to view the predicted discharge destinations and discharge times of the currently admitted patients to facilitate discharge planning. In some implementations, the visualization can specifically identify and/or otherwise call-out patients determined to be complex needs patients, such as patients expected to be discharged to post-acute care facilities. The real-time display can also include additional information that is relevant to discharge planning, such as pending consults, barriers to discharge, insurance details, current unit location, nurse notes, care team activities, disposition trajectory, discharge barriers, and the like. In this regard, the discharge planning tile can provide a concerted view of all the information pertinent to the discharge of the patient. In some embodiments, the discharge planning application can also provide for receiving user feedback regarding discharge barriers, patient needs, scheduled consults, and other relevant information that can affect where and when a patient is discharged. This user feedback can be fed back into the discharge destination and LOS forecasting models to further update and improve the accuracy of these models over time.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Turning now to the drawings, FIG. 1A illustrates a block diagram of an example, non-limiting system 100 for forecasting patient discharge events and needs using machine learning analytics in accordance with one or more embodiments of the disclosed subject matter. Embodiments of systems described herein can include one or more machine-executable components embodied within one or more machines (e.g., embodied in one or more computer-readable storage media associated with one or more machines). Such components, when executed by the one or more machines (e.g., processors, computers, computing devices, virtual machines, etc.) can cause the one or more machines to perform the operations described.

For example, system 100 includes a patient discharge planning module 110, one or more patient input data systems/sources 102, and one or more user devices 122. The patient discharge planning module 110 can be and include various computer/machine executable components, including data collection component 112, care outcomes forecasting component 114 and reporting component 116. These computer/machine executable components (and other described herein) can be stored in memory (not shown) associated with the one or more machines (not shown). The memory can further be operatively coupled to at least one processor (not shown), such that the components (e.g., the discharge planning module 108 itself, the data collection component 112, the care outcomes forecasting component 114, the reporting component 116, and other components described herein), can be executed by the at least one processor to perform the operations described. Examples of said and memory and processor as well as other suitable computer or computing-based elements, can be found with reference to FIG. 17, and can be used in connection with implementing one or more of the systems or components shown and described in connection with FIG. 1 or other figures disclosed herein.

In one or more embodiments, the data collection component 112 can be configured to collect, extract or otherwise receive input data 104 from various patient input data systems/sources 102 for processing by the patient discharge planning module 110 to generate output data 120. For example, the data collection component 112 can collect, from one or more patient input data systems/sources 102, clinical patient data 106 and non-clinical patient data 108 for respective patients admitted to a healthcare facility (e.g., a hospital or the like) at the time of admission and at various points in time over the course of the patients' stay. The care outcomes forecasting component 114 can further processes the input data 104 using one or more machine learning models to forecast patient care outcomes, including but not limited to, expected patient discharge destinations (and placement likelihood), expected patient discharge times (which can include time and data, total forecasted LOS and/or remaining LOS), forecasted readmission risk, and forecasted safety risk.

Figure 1B:
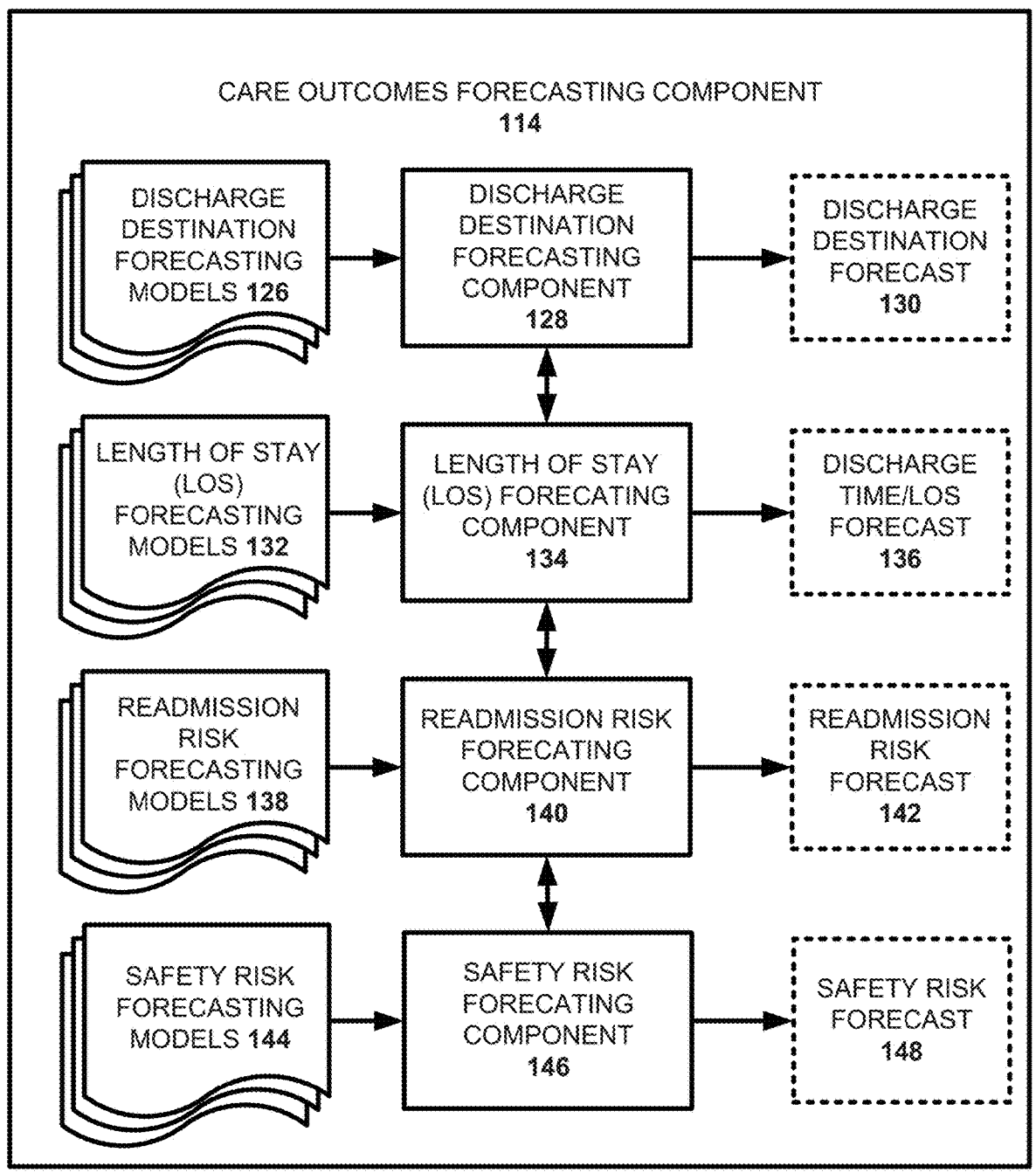
FIG. 1B presents an example care outcomes forecasting component in accordance with one or more embodiments of the disclosed subject matter.

In particular, FIG. 1B provides an example care outcomes forecasting component 114 in accordance with one or more embodiments described herein. In the embodiment shown, the care outcomes forecasting component 114 includes discharge destination forecasting component 128, LOS forecasting component 134, readmission risk forecasting component 140, and safety risk forecasting component 146.

With reference to FIGS. 1A and 1B, in various embodiments, the data collection component 112 can collect, extract or otherwise receive input data 104 including a variety of defined clinal and non-clinical data points associated with an admitted for input to the respective forecasting models (e.g., the one or more discharge destination forecasting models 126, the one or more LOS forecasting models 132, the one or more readmission risk forecasting models 138, the one or more safety risk forecasting models 144, and the like). The data collection component 112 can collect this input data 104 from various different patient input data systems/sources 102 at the time of admission and continue to collect relevant input data from one or more of these patient input data systems/sources 102 over the course of the patient's inpatient stay (e.g., up until discharge or another defined point in the patient's care). For example, the patient input data systems/sources 102 can include various static and dynamics data sources, including electronic databases, systems or devices that provide patient medical records (e.g., EHRs), patient admission information, patient insurance information, patient demographic information, patient family support information, case worker impression information, clinician reports/notes, imaging study information, laboratory information, tracked patient status information, tracked patient vital signs information, tracked clinical event information (e.g., procedures performed, medications administered, etc.), tracked patient location information, and the like. In some embodiments, the data collection component 112 can extract defined clinical and/or non-clinical parameters (and corresponding values) from the input data 104 using natural language processing (NLP). For example, the data collection component 112 can evaluate medical orders, clinical notes, laboratory reports, imaging study reports, dictations, case worker files, etc., using NLP to identify and extract defined input parameters (and values) for input to the respective care outcome forecasting models.

The discharge destination forecasting component 128 can further apply the one or more discharge destination forecasting models 126 to the input data 104 as the input data is received over the course of a patient's stay to generate one or more discharge destination forecasts 130 for the patient over the course of the patient' stay. Likewise, the LOS forecasting component 104 can apply the one or more LOS forecasting models 132 to the input data 104 as the input data is received over the course of the patient's stay to generate one or more discharge time/LOS forecasts 136 for the patient over the course of the patient's inpatient stay. The readmission risk forecasting component 140 can similarly apply the one or more readmission risk models 138 to the input data 104 to generate one or more readmission risk forecasts 142 for the patient, and the safety risk forecasting component 146 can apply the one or more safety risk forecasting models 144 to the input data 140 to generate one or more safety risk forecasts 148 for the patient.

In this regard, the discharge forecasting component 128 can be configured to processes the input data 104 using one or more discharge destination forecasting models 126 to determine or predict one or more discharge destinations where the patients will be discharged. In some implementations, the one or more discharge destination forecasting models 126 can also predict probabilities indicating the predicted probabilities that the patients will be discharged to the respective discharge destinations. For example, for each (or in some implementations one or more) patient evaluated, the discharge destination forecasting component 128 can apply the one or more discharge destination forecasting models 126 to the input data 104 to predict one or more discharge destinations where the patient may possibly or likely be discharged. The one or more discharged forecasting models 120 can also predict the probability that the patient will be discharged to each forecasted discharge destination (e.g., a 90% chance of discharge to a SNF and a 10% chance of discharge home with home assisted care). In this regard, in some implementations, the discharge destination forecasting component 128 can be configured to identify more than one discharge destination where a patient may be discharged. The discharge destination forecasting component 128 can further generate a discharge destination forecast 130 for each (or in some implementations one or more) patient evaluated identifying the discharge destination or destinations where the patient may be discharged and the placement probabilities indicating the expected likelihood that the patient will be discharged to the respective discharge destinations.

The discharge destination forecasting models 126 can thus include one or more machine learning models trained to predict patient discharge destinations and associated probabilities based on learned correlations between defined discharge dispositions/destination and different combinations of clinical and non-clinical features (and/or their feature values). For example, the one or more discharge destination forecasting models 126 can include a model configured to predict an admitted patient's likely and/or possible discharge destination (or destinations) based on a plurality of clinical factors regarding their medical history, their current diagnosis, their scheduled procedures, their tracked vital signs, imaging studies performed (e.g., including modality, timing and results), laboratory studies performed (e.g., including modality, timing and results), as well as a plurality of non-clinical factors, including demographic factors (e.g., age, gender, ethnicity, religion, language, occupation, etc.), socioeconomic factors (e.g., income level, standard of living, tax bracket, current home location, assets, net worth), insurance factors (e.g., whether the patient has insurance and what type of insurance the patient has, whether a detectable has been met, whether reimbursement cap has be met, etc.), post-discharge support factors (e.g., whether the patient lives alone, who the patient lives with if not alone, whether the patient has friends and/or family members responsible for the patient's post discharge care, capabilities of these friends/family members, locations of these friends/family members, etc.), and factors regarding patient post discharge care preferences.

The defined discharge dispositions/destinations can include (but are not limited to): home, home with skilled care (e.g., including different defined types of skilled care), a nursing home, an assisted living facility, a rehabilitation facility, a SNF, a long-term acute care (LTAC) facility, a transitional care unit, a sub-acute hospital, a continuing care retirement community, a Hospice care facility, a palliative care facility, an inpatient acute rehabilitation care facility, a psychiatric care facility, an ambulatory care facility, a respite care facility, and the like, as well as any of these types of facilities or destinations (e.g., home or home with skilled care) that are further subdivided into sub-types based on different specialty services they provide. In this regard, based on learned correlations between discharge of patients to the respective discharge dispositions and different combinations of clinical and non-clinical features, the one or more discharge destination forecasting models 126 can be configured to predict whether, and with what likelihood, a currently admitted patient (e.g., admitted to a hospital or another type of inpatient facility) will be discharged to one or more of the respective discharge dispositions. The discharge destination forecasting component 128 (or the data collection component 112) can thus identify and extract these different clinical and non-clinical features (and/or feature values) as included in the input data 104 for input to the one or more discharge destination forecasting models 126 to determine the predicted discharge destinations (and associated probabilities) for the currently admitted patients. The different clinical and non-clinical patient data features that the one or more discharge destination forecasting models 126, the one or more LOS forecasting models 132, the one or more readmission risk forecasting models 138 and the one or more safety risk forecasting models 144 can be configured to process are discussed in greater detail with reference to FIG. 2.

Thus, in various embodiments, the one or more discharge destination forecasting models 126 can include previously trained/developed models. For example, the one or more discharge destination forecasting models 126 can include one or more models trained on training data including same or similar clinical and non-clinical features included in the input data 104 and recorded discharge information (e.g., discharge document files) identifying actual discharge dispositions where the patients represented in the training data were discharged. It should be appreciated that the model training process can vary based on the type machine learning algorithms employed by the respective discharge destination forecasting models 126, which can vary. For example, some suitable machine learning algorithms/models that can be used for the one or more discharge destination forecasting models 126 can include but are not limited to: a nearest neighbor algorithm, a naïve Bayes algorithm, a decision tree algorithm, a boosting algorithm, a gradient boosting algorithm, a linear regression algorithm, a neural network algorithm, a k-means clustering algorithm, an association rules algorithm, a q-learning algorithm, a temporal difference algorithm, a deep adversarial network algorithm, or a combination thereof. As described in greater detail infra with reference to FIGS. 6-8, in some embodiments, the one or more discharge forecasting models 126 can include a plurality of different models respectively configured to process different types of input parameters, employ different machine learning algorithms, and/or provide different biases toward certain patient groups. In some embodiments, (discussed in greater detail infra with reference to FIG. 13), the one or more discharge destination forecasting models 126 can also be regularly updated/optimized over time based on the input data 104 and discharge information indicating the actual destinations where the patients were actually discharged, as well as user feedback regarding identified discharge barriers for certain patients (e.g., using one or more supervised and/or unsupervised machine learning mechanisms).

The LOS forecasting component 134 can also process the input data 104 using one or more LOS forecasting models 132 to determine or predict one or more discharge times when the respective patients evaluated are expected to be discharged. As used herein, the term "discharge time" can refer to both a calendar date (e.g., day of the week, year, etc.) as well as a specific time of day. In various embodiments, the LOS forecasting component 134 can express the expected discharge time (or times) in terms of LOS, which can include remaining LOS (e.g., remaining number of days until discharge from a current date), and/or expected total LOS (e.g. expected total number of days the patient will be admitted). In some implementations, the one or more LOS forecasting models 122 can also be configured to generate probability information indicating the predicted probability that a patient will be discharged at a forecasted discharge time (e.g., a 70% chance of discharge with a LOS of 3 days and a 30% chance of discharge with a LOS of 4 days). The discharge destination forecasting component 134 can further generate a discharge time/LOS forecast 136 for each (or in some implementations one or more) patient evaluated providing the expected discharge time (or times), remaining LOS, and/or expected total LOS.

In this regard, the LOS forecasting models 132 can include one or more machine learning models that have been trained to predict patient discharge times (and optionally associated probabilities) based on learned correlations between when patients are discharged and a variety of unique combinations of clinical and non-clinical features (and feature values) associated with the patients. The LOS forecasting component 134 (or the data collection component 112) can thus identify and extract these clinical and non-clinical features (and/or feature values) as included in the input data 104 for input to the one or more discharge LOS forecasting models 132 to determine the predicted discharge times (and associated probabilities) for the currently admitted patients. It should be appreciated that the specific input features extracted from the input data 104 by the discharge destination forecasting component 128 and fed into the discharged forecasting models 126 and extracted by the LOS forecasting component 134 and fed into the LOS forecasting models 132 can vary (e.g., the respective models can be configured to process different input sets).

The readmission risk forecasting component 140 can also process the input data 104 using one or more readmission risk forecasting models 138 to determine or predict a readmission risk score for each (or in some implementations one or more) currently admitted patient. The readmission risk score can represent a forecasted probability/likelihood that patient will be readmitted post-discharge. The readmission risk forecasting component 140 can further generate a readmission risk forecast 142 for each (or in some implementations one or more) patient evaluated providing the readmission risk score. In this regard, the readmission risk forecasting models 138 can include one or more machine learning models that have been trained to predict a probability (or another measurable indicator) representing the likelihood a patient will be readmitted based on learned correlations between readmission rates and a variety of unique combinations of clinical and non-clinical features (and feature values) associated with the patients. The readmission risk forecasting component 140 (or the data collection component 112) can further identify and extract these clinical and non-clinical features (and/or feature values) as included in the input data 104 for input to the one or more discharge readmission risk models 138 to determine the readmission risk measures for the currently admitted patients. It should be appreciated that the specific input features extracted from the input data 104 by the readmission risk forecasting component 140 and fed into the readmission risk forecasting models 138 can be the same or vary from those extracted and applied to the discharged forecasting models 126 and the LOS forecasting models 132.

Similarly, the safety risk forecasting component 146 can also process the input data 104 using one or more safety risk forecasting models 144 to forecast information regarding safety risks associated with each (or in some implementations one or more) currently admitted patient. In this regard, although hospitals, clinics, and doctor's offices take many steps to keep their patients safe, medical errors, also referred to as adverse events, can happen. In some embodiments, the one or more safety risk forecasting models 144 can forecast safety risks identifying specific adverse events that may occur for the patient and/or be caused by the patient and likelihood of occurrence (e.g., this patient has an X % probability of acquiring an infection). In some embodiments, the one or more safety risk forecasting models 144 can forecast a safety risk score representative of a collective safety degree of risk representative of the likelihood of occurrence of adverse events attributed to the patient and/or severity of the adverse events. The safety risk forecasting component 146 can further generate a safety risk forecast 148 for each (or in some implementations one or more) patient evaluated providing the forecasted adverse events, likelihood of occurrence of the adverse events and/or the safety risk score.

In this regard, the safety risk forecasting models 144 can include one or more machine learning models that have been trained to predict adverse events or safety risks that may occur and/or the probability (or another measurable indicator) representing the likelihood of occurrence based on correlations between the adverse events/safety risks and a variety of unique combinations of clinical and non-clinical features (and feature values) associated with the patients. The safety risk forecasting component 146 (or the data collection component 112) can further identify and extract these clinical and non-clinical features (and/or feature values) as included in the input data 104 for input to the one or more safety risk models 144 to determine the safety risks (and associated probabilities of occurrence) for the currently admitted patients. The safety risk forecasting component 146 can also generate a safety risk score representative of the cumulative degree of safety risk (e.g., as a function of the collective safety risks identified, the likelihood of occurrence, and/or risk severity associated with the types of the safety risks). It should be appreciated that the specific input features extracted from the input data 104 by the safety risk forecasting component 146 and fed into the safety risk forecasting models 144 can be the same or vary from those extracted and applied to the discharged forecasting models 126, the LOS forecasting models 132, and/or the readmission risk forecasting models 138.

The type of machine learning algorithms/models used for the LOS forecasting models 132, the readmission risk forecasting models 138 and the safety risk forecasting models 144 can also vary. For example, some suitable machine learning algorithms/models that can be used for the one or more LOS forecasting models 132, the readmission risk forecasting models 138, and the safety risk forecasting models 144 can include but are not limited to: a nearest neighbor algorithm, a naïve Bayes algorithm, a decision tree algorithm, a boosting algorithm, a gradient boosting algorithm, a linear regression algorithm, a neural network algorithm, a k-means clustering algorithm, an association rules algorithm, a q-learning algorithm, a temporal difference algorithm, a deep adversarial network algorithm, or a combination thereof. As described in greater detail infra with reference to FIGS. 6-8, in some embodiments, the LOS models 132, the readmission risk forecasting models 138 and the safety risk forecasting models 144 can also include a plurality of different models respectively configured to process different types of input parameters, employ different machine learning algorithms, and/or provide different biases toward certain patient groups. The LOS forecasting models 132, the readmission risk forecasting models 138 and the safety risk forecasting models 144 can also be regularly updated/optimized over time based on the input data 104 and discharge information indicating the actual discharge times (e.g., expressed in terms of LOS) when the patients were actually discharged, as well as user feedback regarding identified discharge barriers for certain patients (e.g., using one or more supervised and/or unsupervised machine learning mechanisms).

With reference again to FIG. 1A in view of FIG. 1B, the reporting component 116 can further facilitate providing output data 120 regarding the predicted care outcomes 122, (e.g., including the discharge destination forecasts 130, the discharge time/LOS forecasts 136, the readmission risk forecasts 142, and the safety risk forecasts 148) to one or more relevant entities (e.g., systems, devices, applications, etc.) as the predicated care outcome information is generated in real-time. The output data 120 can be reported using various suitable data structures (e.g., as machine readable text, as human readable text, as a graphical visualization, etc.) and/or electronic rendering applications. For example, in some embodiments, the reporting component 116 (and/or the discharge planning module 108) can be integrated with or be coupled to one or more applications that provide various features and/or functionalities associated with optimizing care delivery and/or discharge planning. For instance, in one implementation, the application can include care delivery optimization application accessible via a network-based platform (e.g., a web-application, a website, a thin client application), a centralized command center, or another suitable operating environment. The display component 118 can further provide one or more tiles reporting the output data 120 in real-time.

For example, in the embodiment shown, the reporting component 116 can include a display component 118 configured to facilitate generating a graphical visualization and/or graphical user interface (GUI) for displaying at one or more user devices 122 that includes information regarding forecasted patient outcomes for one or more currently admitted patients. The forecasted predicted care outcomes 122 information can include for example, for each (or in some implementations one or more) of the currently admitted patients, information identifying the predicted discharge destinations and likelihoods, the predicted discharge time (or remaining LOS), the predicted readmission risk, the predicted safety risk, and the like. The one or more user devices 122 can include for example, display monitors and/or computing devices associated with entities involved in the patients' inpatient and/or post-discharge care (e.g., clinicians at the inpatient facility, administrative workers at the inpatient facility, case workers, discharge planners, the patients themselves, friends and family of the patients, etc.). In this regard, the visualization can allow a care provider, case worker, or the like, to view the predicted discharge destinations and discharge times of the currently admitted patients to facilitate discharge planning. In accordance with this example, displayed information regarding the forecasted patient outcomes can be dynamically updated in real-time to reflect updated predictions determined over the course of the patients' inpatient stay.

In this regard, the deployment architecture of system 100 and other systems described herein can vary. For example, various features and functionalities of system 100 (and additional systems described herein) can be deployed using a distributed computing environment, wherein the one or more devices, sources, modules and/or components of system 100 (and other systems described herein) can be provided in a distributed manner across various interconnected (via one or more networks) systems and devices (e.g., internal systems, the cloud, two or more dedicated servers, etc.). For example, system 100 can be deployed in a cloud architecture, a virtualized enterprise architecture, or an enterprise architecture wherein one the front-end components and the back-end components are distributed in a client/server relationship. With these embodiments, one or more features and functionalities of the system 100 can be deployed as a web-application, a cloud-application, a thin client application, a thick client application, a native client application, a hybrid client application, or the like, wherein one or more of the front-end components (e.g., reporting component 116) are provided at client device (e.g., the one or more user devices 122) and one or more of the back-end components (e.g., the data collection component 112, care outcomes forecasting component 114, etc.) are provided in the cloud, on a virtualized server, a virtualized data store, a remote server, a remote data store, a local data center, etc., and accessed via a network (e.g., the Internet). In this regard, the patient input data systems/sources 102, the patient discharge planning module 110, one or more components of the patient discharge planning module 110, and/or the one or more user devices 122 can be physically separated yet communicatively coupled via one or more networks. However, it should be appreciated however that system 100 is not limited to this architectural configuration. For example, in another embodiment, the entirety of the patient discharge planning module 110 can be deployed on a single local device (e.g., a desktop computer) as a local web-based application.

Figure 2:
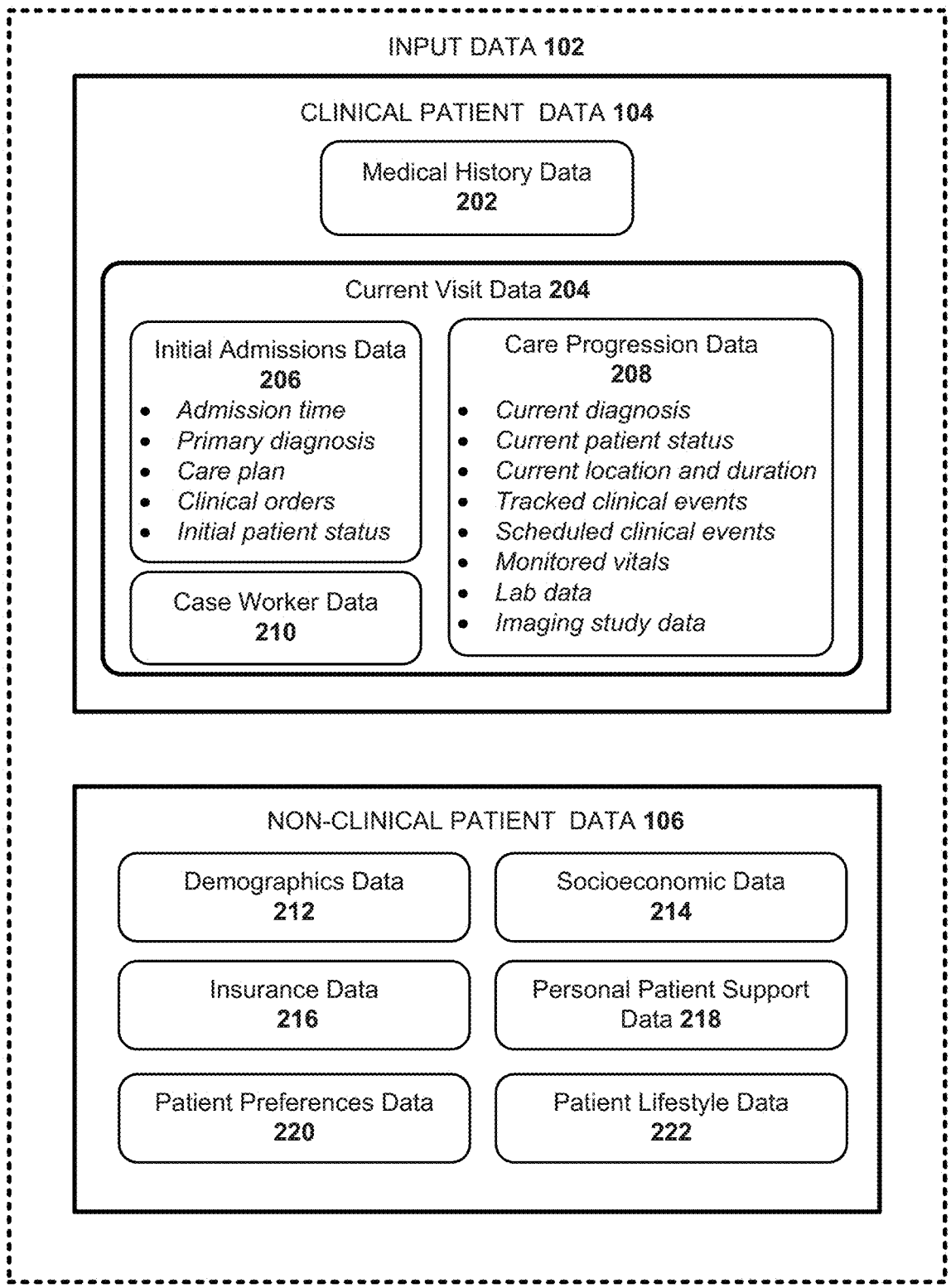
FIG. 2 provides example types of clinical and non-clinical patient data that can be used as input to forecast patient discharge events and needs in accordance with one or more embodiments of the disclosed subject matter.

Turning now to FIG. 2, presented are some example types of clinical patient data 106 and non-clinical patient data 108 that can be used as input to forecast patient discharge events and needs in accordance with one or more embodiments of the disclosed subject matter. In this regard, the one or more discharge destination forecasting models 126 and/or the one or more LOS forecasting models 132, the one or more readmission risk forecasting models 138, and the one or more safety risk forecasting models 144 can respectively be configured to predict their corresponding care outcomes based on a plurality of defined clinical features included in the clinical patient data 106 and defined non-clinical features included in non-clinical patient data 108.

With reference to FIG. 2 in view of FIGS. 1A and 1B, in one or more embodiments, the clinical patient data 106 can be grouped into medical history data 202 and current visit data 204. The medical history data 202 can include medical history information for currently admitted patients and past patients, such as that provided in by one or more EHR databases and systems. For example, the patient medical history information can include internal medical history information for patients associated with a single healthcare organization, as well as medical history information aggregated for patients across various disparate healthcare organizations/vendors (e.g., internal and third-party organizations/vendors) and accessed via a healthcare information exchange system (HIE). Some clinical features included in the medical history data 202 that can be used as input to one or more discharge destination forecasting models 126, the one or more of LOS forecasting models 132, the one or more readmission risk forecasting models 132 and/or the one or more safety risk forecasting models 144 can include but are not limited to: comorbidities, ongoing illnesses (including mental illnesses), past diagnoses, past hospital stays and associated LOS, past intensive care unit (ICU) stays, past surgeries, regular and acute medications taken, and whether the patient has any implanted medical devices (IMDs) and if so, the type and location of the IMDs.

The current visit data 204 can include clinical information regarding a patient's current inpatient stay from the time of admission to the time of discharge. The current visit data 204 is divided into initial admissions data 206, care progression data 208 and case worker data 210. The initial admissions data 206 can include known clinical information about a patient collected at or near the time of admission of the patient, including information regarding the context of admission (e.g., where, when, and why the patient was admitted), the state of the patient at or near the time of admission, and the initial clinical care ordered and/or provided to the patient at or near the time of admission. Some clinical features included in the initial admissions data 206 that can be used as input to the one or more discharge destination forecasting models 126, the one or more of LOS forecasting models 132, the one or more readmission risk forecasting models 132 and/or the one or more safety risk forecasting models 144, can include but are not limited to: admission time, admission entry point (e.g., emergency room, elective, transfer, scheduled surgery, etc.), primary diagnosis, initial treatment provided (e.g., surgical procedures, diagnostic tests, medications administered, etc.), initial clinical orders, patient status and reported symptoms upon admission, initial care plan or care pathway prescribed, and the like. In some implementations, the initial admissions data can also include a measure of medical complexity, severity or risk determined for the patient which can be used as input to the respective care outcome forecasting models. The initial admission data can be received from various sources or systems. For example, the initial admissions data 206 can be provided by and/or extracted from (e.g., via the collection component 110) admission forms (e.g., filled out by the patient or another person accompanying the patient), from clinical data entry systems, from clinical notes (e.g., written, spoken and recorded, etc.), from electronic scheduling systems (e.g., providing information regarding scheduled procedures and clinical events), and the like.

The care progression data 210 can include clinical information regarding a patient's status, location, and treatment over the course of the patient's stay. In this regard, the care progression data 208 can provide a timeline of the patient's stay that tracks relevant information regarding the clinical treatment received and scheduled, the patient's status, and the patient's location (e.g., care unit) as a function of time. Some clinical features included in the care progression data 208 that can be used as input to the one or more discharge destination forecasting models 126, the one or more of LOS forecasting models 132, the one or more readmission risk forecasting models 132 and/or the one or more safety risk forecasting models 144, can include but are not limited to: current diagnosis, current patient status, current patient location and duration at that location, medical treatment received (e.g., procedures performed, medications administered, etc.), clinicians involved in provision of the treatment (e.g., ordering physician, attending physician, nurses, etc.), laboratory tests conducted (e.g., including type, timing and results reported), imaging studies performed (e.g., including type, timing and results reported), other diagnostic tests performed, unit transfers, and occurrence of other defined medical events. In various embodiments, this care progression data 208 can be reported and received in real-time over the course of the patient's stay. For example, this care progression data can be provided by and/or extracted from (e.g., via the collection component 110), from clinical data entry systems, from clinical notes (e.g., written, spoken and recorded, etc.), from electronic scheduling systems (e.g., providing information regarding scheduled procedures and clinical events), from clinical ordering systems, from medical imaging systems, from laboratory reporting systems, and the like.

The care progression data 208 can also include tracked physiological parameters regarding a patient's physiological state (e.g., vital signs and other measurable physiological parameters) captured at one or more timepoints over the course of the patient's stay. In various embodiments, these physiological parameters can be received in real-time (or substantially real-time) from one or more medical monitoring devices, biofeedback devices and/or audio/visual monitoring devices.

Figure 3:
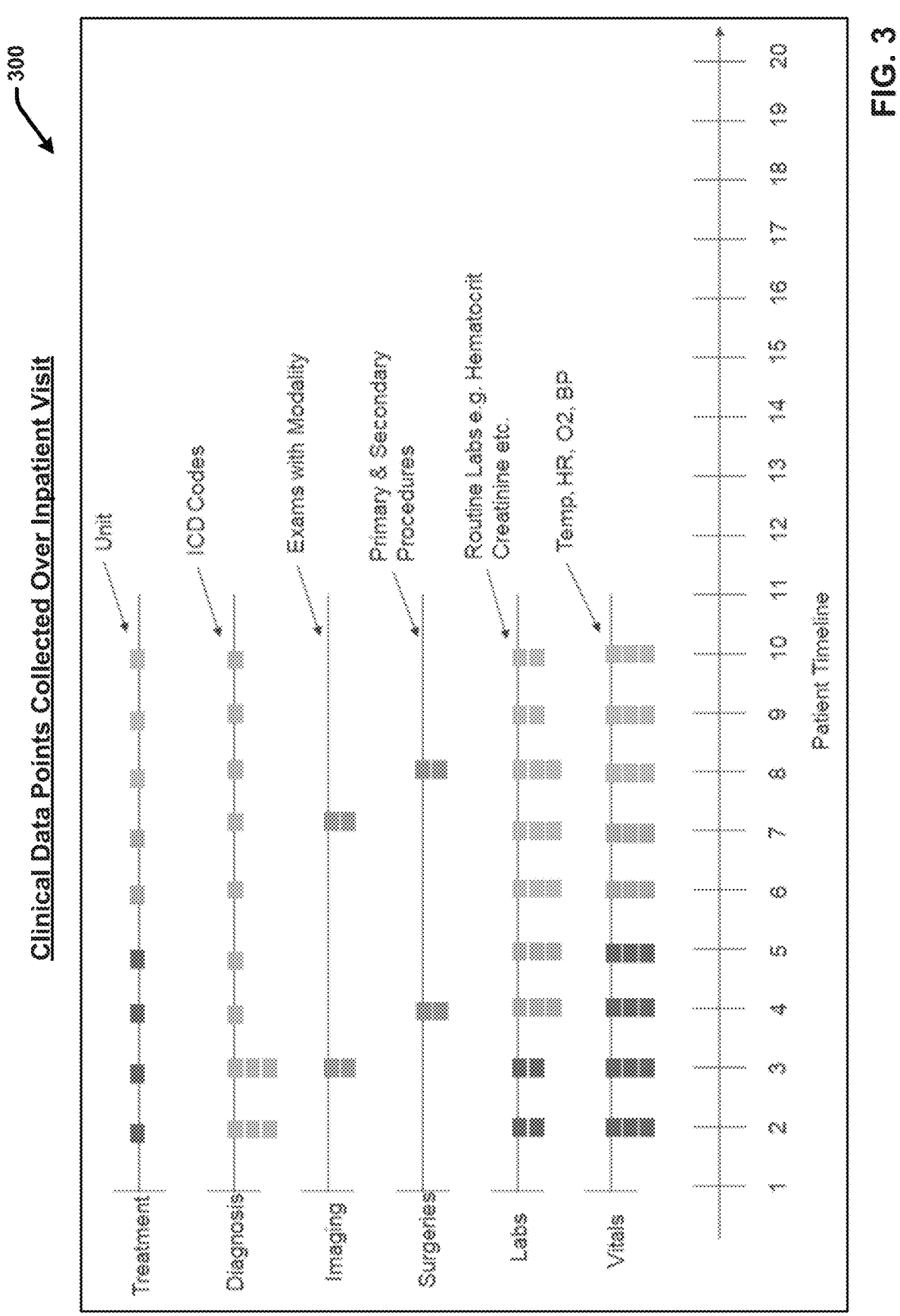
FIG. 3 presents example clinical data points that can be collected for a patient over an inpatient stay in accordance with one or more embodiments of the disclosed subject matter.

For example, FIG. 3 presents a chart 300 that provides some example clinical data points that can be collected as care progression data 208 for a patient over an inpatient stay in accordance with one or more embodiments of the disclosed subject matter. In accordance with the example shown in chart 300, the clinical data points tracked include treatment unit, diagnosis, imaging studies performed (e.g., including type/modality), surgeries performed, laboratory tests performed and the results (e.g., hematocrit, creatinine, etc.), and patient vitals. These parameters are tracked as a function of time (e.g., which can be in hours, days, or another suitable sampling frequency). For example, each square along the treatment unit timeline can represent a specific unit where the patient was located at the corresponding time. The respective squares along the diagnosis timeline can represent a specific diagnosis code that corresponds the patient's diagnosis (or diagnoses) at the corresponding time. The respective square along the imaging timeline can represent a specific type of imaging study (including modality) that was performed at the corresponding time. For example, certain types of imaging studies are more costly, more invasive, and/or more disruptive (e.g., with respect to radiation exposure) than others, and are only performed if warranted given the context of the patient's medical needs and state. Thus, the specific types of imaging studies performed and the respective times at which they are performed can correlate to the patient's medical needs and state which can further correlate to the patient's discharge disposition, LOS, readmission risk, and/or safety risks.

The respective squares along the surgeries timeline can further represent a particular type of surgical procedure (or another non type of procedure if not surgical) performed at the corresponding time. Each square along the labs timeline can represent a specific type of laboratory reading that was conducted and values of the measured parameter(s). Similarly, each square along the vitals timeline can represent a different measured physiological parameter and the corresponding parameter value captured at the respective times.

In various embodiments, the one or more discharge destination forecasting models 126, the one or more of LOS forecasting models 132, the one or more readmission risk forecasting models 132 and/or the one or more safety risk forecasting models 144, can be configured to process these data points as input (e.g., and other parameters described herein, including medical history data 204 parameters, initial admission data 206 parameters, case worker data 210 parameters, and various non-clinical patient data 108 parameters) to predict the monitored patient's care outcomes (e.g., the discharge trajectory including one more discharge destinations and corresponding likelihood of placement there, expected discharge time/date or total LOS, readmission risk and/or safety risks). For example, in some implementations, the data collection component 112 can collect receive, or otherwise extract these data points over the course of a patient's care. The discharge destination forecasting component 128, the LOS forecasting component 134, the readmission risk forecasting component 140 and/or the safety risk forecasting component 146 can further establish defined sets or groups of the data points for input to their respective models, wherein each defined set or group of the data points reflects a period of time up to the current point in time at which the models are applied.

For example, the discharge destination forecasting component 128 can be configured to apply the one or more discharge destination forecasting models to a first set of input parameters reflective of the data points collected from time (t0) to time (t1) to generate a first discharge destination forecast. After some time passes and additional data points are received, the discharge destination forecasting component 128 can be configured to apply the one or more discharge destination forecasting models to a second set of input parameters reflective of the data points collected from time (t0) to time (t2) to generate a second (updated) discharge destination forecast that reflects all the data points collected thus far, and so on. The LOS forecasting component 134 can apply the one or more LOS forecasting models to data sets collected in a same or similar fashion. The reporting component 116 can further report the most up to date discharge trajectory forecast and/or LOS forecast.

In some implementations, the frequency at which the models are applied can be fixed (e.g., every 30 minutes, every hour, every 24 hours, every 48 hours, etc.). In other implementations, the discharge destination forecasting component 128, the LOS forecasting component 134, the readmission risk forecasting component 140 and/or the safety risk forecasting component 146 can be configured to apply their respective models in response to reception of a new data point reflective of the occurrence of a new clinical event for a monitored patient (e.g., a unit transfer, a surgery performed, an imaging study conducted, etc.) and/or a significant change (e.g., relative to a defined degree of change) in a previously monitored parameter (e.g., a spike in temperature, a decrease in heart rate (HR), etc.).

In some embodiments, the discharge destination forecasting component 128, the LOS forecasting component 134, the readmission risk forecasting component 140 and/or the safety risk forecasting component 146, can calculate certain input parameter values that involve a time component based on the data points collected up to a current point in time (e.g., at which the models are applied) as appropriate. For example, in some implementations, the model input parameter values can include a duration of time associated with a monitored parameter (e.g., duration of time in the ICU unit, duration of time between surgeries, etc.), a frequency associated with a monitored parameter (e.g., frequency of procure X, number of imaging studies performed, etc.), and/or a degree of change/variance in a monitored parameter. With these embodiments, the discharge destination forecasting component 128, the LOS forecasting component 134, the readmission risk forecasting component 140 and/or the safety risk forecasting component 146, can calculate the parameter input values based on the received data points prior to input into their respective models.

With reference again to FIG. 2, the case worker data 210 can include information provided by a case worker (or the like) that is involved with a patient's care. The case worker data can be received and extracted from notes, files, reports and the like provided by the case worker over the course of the patient's inpatient stay. For example, some patients, particularly complex needs patients, can be assigned a case worker to serve as a liaison for the patient and the different services they receive in and out of the hospital. Case workers can perform tasks including determining initial discharge plans and tracking and coordinating care activities, such as arranging dialysis for a patient post discharge. The case worker often works with the patient and the service provides in the community to coordinate and arrange these care activities. Case workers can also provide feedback regarding a patient's care needs, behaviors, capabilities (e.g., capabilities to care for oneself), and mental status. For example, a case worker can report information regarding specialty care requirements of a patient, such as whether a patient requires ventilator care, hemodialysis, chemotherapy, radiation therapy, wound vacuums, and/or has mental health care needs. In another example, a case worker can report information regarding a specialty diet of a patient, whether a patient requires medical shots to be administered, whether a patient has bandage change needs, and the like. Case workers further provide documentation regarding their involvement in the patient's care (e.g., as notes, activity logs, formalized reports, or the like). For example, case workers can provide documentation regarding their discharge plans, coordinated care activities, and observed patient care needs, behavior, capabilities, mental status, etc. In this regard, some clinical features included in the case worker data 210 that can be extracted from the case worker documentation and used as input to the one or more discharge destination forecasting models 126, the one or more of LOS forecasting models 132, the one or more readmission risk forecasting models 138 and/or the safety risk forecasting models 144, can include but are not limited to: patient care needs, medical equipment needs, care activities scheduled, care activities performed, recommended discharge disposition, discharge activities scheduled, transportation arrangements, patient capabilities, patient mental status, patient behaviors, and the like.

The non-clinical patient data 108 can include various additional features that can influence or indicate the type of post discharge care a patient will need and/or can obtain from a personal, social, logical, economic and family support perspective. For example, in the embodiment shown, the non-clinical patient data 108 can include demographics data 212, socioeconomic data 214, insurance data 216, personal patient support data 218, patient preferences data 220 and patient lifestyle data 222.

The demographics data 212 can include several demographic features about a patient, such as those provided in admit, discharge and transfer (ADT) feeds, EHR databases and systems, admission forms, and the like. Some non-clinical features included in the demographics data 212 that can be used as input to the one or more discharge destination forecasting models 126, the one or more of LOS forecasting models 132, the one or more readmission risk forecasting models 138 and/or the safety risk forecasting models 144, can include but are not limited to: patient age, gender, height, weight, body mass index (BMI), ethnicity/race, religion, language, marital status, nationality, birth location (e.g., country, state and/or city), and current residence location (e.g., country, state and/or city).

The socioeconomic data 214 can include social and economic factors about a patient. For example, some non-clinical features included in the socioeconomic data 214 that can be used as input to the one or more discharge destination forecasting models 126, the one or more of LOS forecasting models 132, the one or more readmission risk forecasting models 138 and/or the safety risk forecasting models 144, can include but are not limited to: education level, occupation, income level per capita, median household income, debt, net worth, credit score, assets, home zip code, rural-urban community area (RUCA) code associated with the patient's current home location, criminal background (e.g., arrests, convictions, etc.), living family members (e.g., spouse, parents, grandparents, siblings, children, grandchildren), family member ethnicities, number of siblings, number of children, number of grandchildren, next of kin, emergency contact type, emergency contact person, and the like.

The insurance data 216 can include information regarding a patient's medical insurance, (including whether the patient has medical insurance), that can control if a patient can receive certain services, where they can receive them, costs of services, and the like. In this regard, some non-clinical features included in the insurance data 216 that can be used as input to the one or more discharge destination forecasting models 126, the one or more of LOS forecasting models 132, the one or more readmission risk forecasting models 138 and/or the safety risk forecasting models 144, can include but are not limited to: whether the patient is insured or uninsured, insurance provider, insurance plan type, and parameters regarding plan coverage benefits and restrictions.

The personal patient support data 218 can include information regarding who (if anyone besides that patient), will be responsible for caring for the patient from the point of discharge. This can include family, friends, case workers, or another individual (or group of individuals) that is hired or volunteered help. In some implementations, the personal patient support data 218 can also include information regarding the patient's home environment or living arrangements (e.g., including type, structural features such as stairs/elevators, location, and other individuals that live there). The personal patient support data 218 can also include factors regarding capabilities of the patient to care for oneself post-discharge. In this regard, some non-clinical features included in the personal patient support data 218 that can be used as input to the one or more discharge destination forecasting models 126, the one or more of LOS forecasting models 132, the one or more readmission risk forecasting models 138 and/or the safety risk forecasting models 144, can include but are not limited to: whether the patient has anyone that will be responsible for the patient post-discharge, relationship of the person or persons responsible for the patient to the patient (e.g., friend, family member, type of family member), age of person or persons responsible for the patient, whether the patient has transportation, whether the patient lives alone, who lives with the patient (e.g., friends, family members, live in nurse, etc.), type of home environment (e.g., house, apartment), location of home environment, whether the home environment requires the patient to use stairs or an elevator, whether the patient is capable of performing daily life activities (e.g., feeding oneself, bathing oneself, clothing oneself, etc.), and mobility of the patient (e.g., ability to walk, requires a walker, requires crutches, requires a wheelchair, etc.).

The patient preferences data 220 can include patient preferences regarding where, when, how and by whom the patient would prefer to receive various medical services. For example, some non-clinical features included in the patient preferences data 220 that can be used as input to the one or more discharge destination forecasting models 126, the one or more of LOS forecasting models 132, the one or more readmission risk forecasting models 138 and/or the safety risk forecasting models 144, can include but are not limited to: preferred discharge destination, preferred providers, preferred scheduling times for appointments, and preferred characteristics of the caregivers involved in the patient's care.

The patient lifestyle data 222 can include information regarding patient lifestyle activities and behaviors that can have an impact on the patient's medical condition or state during and after discharge. For example, some non-clinical features included in the patient preferences data 220 that can be used as input to the one or more discharge destination forecasting models 126, the one or more of LOS forecasting models 132, the one or more readmission risk forecasting models 138 and/or the safety risk forecasting models 144, can include but are not limited to: frequency/amount of tobacco smoking, frequency/amount of alcohol use, frequency/amount and type of other recreational drug use, frequency/amount and type of exercise, recent foreign travel, and exposure to environmental pathogens through recreational activities or pets.

Figure 4:
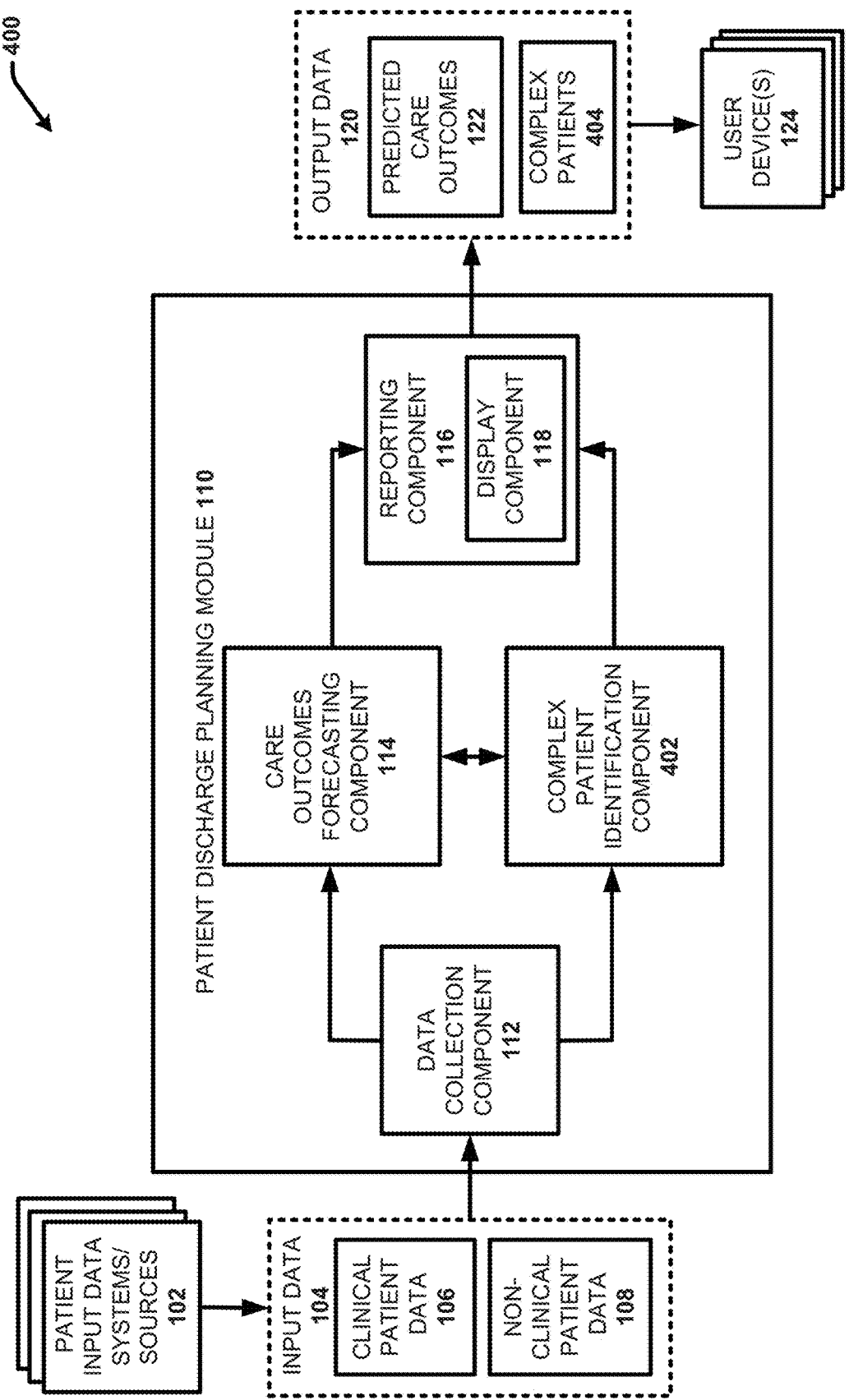
FIG. 4 illustrates a block diagram of another example, non-limiting system for forecasting patient discharge events and needs using machine learning analytics in accordance with one or more embodiments of the disclosed subject matter.

FIG. 4 illustrates a block diagram of another example, non-limiting system 400 for forecasting patient discharge events and needs using machine learning analytics in accordance with one or more embodiments of the disclosed subject matter. System 400 includes same or similar features as system 100 with the addition of complex patient identification component 402 to the patient discharge planning module 110 and information regarding complex patients 404 to the output data 120. Repetitive description of like elements employed in respective embodiments is omitted for sake of brevity.

In one or more embodiments, the complex patient identification component 402 can identify currently admitted patients that are considered to be complex needs patients and/or expected to become complex needs patients (also generally referred to herein as "complex patients"). In this regard, a portion of the patients currently admitted to a hospital (or another inpatient facility) can be considered complex needs patients. These patients require more care and resources during their hospital stay and after their discharge from the hospital. Identifying such type of patients early and managing their care during their hospital stay and after their discharge can significantly improve the care delivery for these patients. This will lead to reduced readmissions and hospital stays. However, identifying such patients early faces multiple challenges.

The complex patient identification component 402 can employ various techniques to identify complex needs patients early into their admission based on the unique array of clinical and non-clinical input parameters discussed herein (with reference to FIG. 2). In some embodiments, the complex patient identification component 402 can employ machine learning methods, qualitative methods or combination thereof (e.g., a hybrid of machine learning and qualitative methods), to identify complex patients based on the forecasts generated by the care outcomes forecasting component 114 (e.g., the discharge destination forecasts 130, the discharge time/LOS forecasts 136, the readmission risk forecasts 142 and the safety risk forecasts 148). With these embodiments, the complex patient identification component 402 can employ the output of the care outcomes forecasting component 114 to identify patients that are or are likely to become complex needs patients. In other embodiments, the complex patient identification component 402 can employ machine learning methods, qualitative methods or combination thereof (e.g., a hybrid of machine learning and qualitative methods), to identify complex patients based on defined clinical and non-clinical parameters extracted from the input data 104 (e.g., parameters regarding medical complexity, socio-economic conditions, insurance, medications, behavioral characteristics, mental health characteristics, etc.).

In this regard, in some implementations, the complex patient identification component 402 can determine whether a currently admitted patient is a complex needs patient (or not) based on their forecasted discharge destination(s) and placement probability. For example, certain defined discharge destinations can be associated with complex needs patients. In one implementation of this embodiment, the complex needs patient identification component 402 can classify all patients that receive a predicted discharge destination to one that is associated with complex needs patients, as complex needs patients. For example, the complex patient identification component 402 can classify all patients that receive a forecasted discharge destination to a LTAC disposition as complex needs patients based on previously defined information associating the LTAC disposition with complex needs patients. In another implementation, the complex patient identification component 402 can also determine whether a patient is a complex needs patient based on whether the predicted probability of the patient being discharged to a disposition included in the complex needs group is above a defined probability threshold. For example, the complex patient identification component 402 can classify all patients that receive a forecasted discharge destination to a LTAC disposition with a probability of 70% or higher as complex needs patients based on previously defined information associating the LTAC.

In another embodiment, in addition to, (or alternative to), determining whether a currently admitted patient is or is likely to become a complex needs patient based on their discharge destination forecast 130, the complex patient identification component 402 can determine whether a patient is considered a complex needs patient or likely to become a complex needs patient based on a variety of other criteria. For example, in some implementations, the other criteria can include the patient's discharge time forecast 136, patient readmission risk forecast 142 and/or the patients safety risk forecast 148. In another implementation, the other criteria can include one or more of the clinical and non-clinical factors discussed herein with reference to FIG. 2, including but not limited to: one or more medical history factors discussed herein, one or more initial admissions data factors discussed herein, one or more care progression data factors discussed herein, one or more case worker data factors discussed herein, one or more demographic factors discussed herein, one or more socioeconomic factors discussed herein, one or more insurance factors discussed herein, one or more personal patient support factors discussed herein, one or more patient preferences factors discussed herein and/or one or more patient lifestyle factors discussed herein. In this regard, as the data collection component 112 collects, extracts or otherwise receives input data 104 about a currently admitted patient over the course of the patient's stay and/or the care outcomes forecasting component 114 generates predicated care outcomes data (e.g., discharge destination forecasts 130), discharge time forecasts 136, patient readmission risk forecasts 142 and/or the patients safety risk forecast 148), the complex patient identification component 402 can evaluate and reevaluate the aggregated data to determine whether the patient is or is likely to be considered a complex needs patient.

In some implementations of these embodiments, the complex patient identification component 402 can employ one or more machine learning techniques to learn correlations between the various discharge care outcomes (e.g., discharge destinations and associated probabilities, LOS, readmission risk, safety risks, etc.), clinical factors, and non-clinical factors described herein and patients historically considered complex needs patients to facilitate determining whether a currently admitted patient should be classified as a complex needs patient. For example, the complex patient identification component 402 can learn correlations between discharge destinations, LOS, readmission risk, and/or safety risks, to a patient being classified as complex needs. In another example, the complex patient identification component 402 can learn what specific combinations of the clinical and non-clinical parameters (and the parameter values) included in the input data 104 correlate to a patient considered to be complex needs. The complex patient identification component 402 can further develop one or more complex patient classification models configured to classify a patient as complex needs or not based on the learned correlations. The complex patient identification component 402 can further apply the one or more classification models to the input data 104 collected for an admitted patient (and in some implementations the predicted discharge dispositions/probabilities and LOS values determined for the patient) to classify the patient complex needs or not.

In another embodiment, the complex patient identification component 402 can filter the currently admitted patients based on their forecasted discharge destination, LOS, readmission risk and/or safety risks, or another defined criterion (e.g., medical complexity, diagnosis, comorbidity, etc.) to generate a smaller more refined subgroup of patients to evaluate for classification as complex needs or not. For example, the complex needs classification component 402 can filter out all patients predicted to be discharged home or select only those patients predicted to be discharged to one or more defined post-acute care dispositions that generally receive complex needs patients. The complex needs classification component 402 can also filter and select the currently admitted patients based on the LOS exceeding a defined number of days. With these embodiments, the complex needs classification component 402 can then evaluate only the filtered subgroup of patients based on one or more additional defined criteria (e.g., clinical and/or non-clinical factors) and/or using the one or more classification models to determine which patients included in the subgroup to classify as complex needs.

In another embodiment, the complex patient identification component 402 can be configured to identify complex needs patients using machine learning, qualitative and/or hybrid techniques based on defined clinical and non-clinical factors extracted from the input data 104 (e.g., including parameters regarding medical complexity, socio-economic conditions, insurance, medications, behavioral characteristics, mental health characteristics, etc.). The care outcomes forecasting component 114 can further be configured to only evaluate those patients classified as complex needs patients to determine predicted care outcomes 122 for those patients. With these embodiments, the respective care outcomes forecasting models (e.g., the one or more discharge destination forecasting models 126, the one or more LOS forecasting models 132, the one or more readmission risk forecasting model 138, and/or the one or more safety risk forecasting models 144), can be specifically trained/configured to evaluate input parameters (and associated values) for the target patient population of complex needs patients.

In some embodiments, the complex patient identification component 402 can also employ machine learning methods, qualitative methods, or hybrid techniques to identify relevant clinical factors collected for a currently admitted patient (e.g., via the data collection component 112) that strongly influence the patient being classified as complex needs and/or that require clinical attention (e.g., during the patient stay and/or post-discharge). For example, the complex patient identification component 402 can identify specific care needs of the complex patient that significantly contribute (e.g., relative to other factors) to them being classified as complex (e.g., needing hemodialysis, chemotherapy, radiation therapy, wound vacuums, and mental health care needs, having a physical disability, etc.). In another example, the complex patient identification component 402 can identify clinical factors that require coordination and scheduling for the complex needs patient during and/or post-discharge (e.g., the patient needs dialysis before and after discharge along with nursing support, the patient needs oxygen before and after discharge along with equipment support etc.). These relevant factors can be predefined and/or learned using one or more machine learning techniques. In some implementations, these strong contributing factors can be given higher weight in the complex needs classification model.

The reporting component 116 can further include information regarding those currently admitted patients classified as complex in the output data 120. For example, in the embodiment shown, this information is depicted as complex patients 404 information. In some implementations, if determined, the complex patient 404 information can also include information describing the relevant clinical factors that strongly influence the patient being classified as complex and/or require clinical attention. In some embodiments in which the output data 120 is presented in a display tile (e.g., as a visualization or GUI) at one or more user devices 122 to entities involved in the patients care, the display component 118 can visually distinguish or otherwise call attention to those patients classified as complex. In this regard, complex patients can be flagged or otherwise called to attention to facilitate better managing and coordinating their care needs during and after their inpatient stay.

Figure 5:
FIG. 5 presents an example visualization reporting identified complex patients and their forecasted discharge dispositions in accordance with one or more embodiments of the disclosed subject matter.

For example, FIG. 5 presents an example visualization 500 reporting identified complex patients and their forecasted discharge dispositions in accordance with one or more embodiments of the disclosed subject matter. Visualization 500 provides an example display that can be generated by the display component 118 based on the output data 120 as generated/determined using the techniques described herein. In the embodiment shown, the visualization 500 identifies three currently admitted patients (names abbreviated) that have been classified as complex patients and forecasted to need post-acute placement. The left side of the visualization 500 provides some high-relevant information for each patient, including their medical record number (MRN), current department and unit number (e.g., medical (MED), neurological (NEURO), and insurance (INS) provider. As shown in FIG. 5, in some implementations, uninsured patients can be flagged. The visualization also includes information identifying the respective patients' admission (ADM) date, current LOS, and estimated departure date (EDD). As shown in FIG. 5, in some implementations, uninsured patients without an EDD can be flagged. The visualization also includes symbols that respectively represent medical reasons contributing to their classification as a complex needs patient. In other implementations, text descriptions can be used instead and/or in addition to the symbols. The left side of the visualization 500 further provides information regarding the forecasted discharge dispositions of the respective patients and probabilities indicating the expected likelihood of discharge to the respective dispositions. The far-right side of the visualization further includes the discharge dispositions predicted for the respective patients and associated placement probabilities indicating the likely of placement. The predicted discharge dispositions include a skilled nursing facility (SNF), long-term acute care (LTAC), and rehabilitation (REHAB). In this regard, with this example, two different discharge dispositions are predicted for each patient. However, in practice, the number of discharge dispositions predicted for each patient can vary from one or more.

Figure 6:
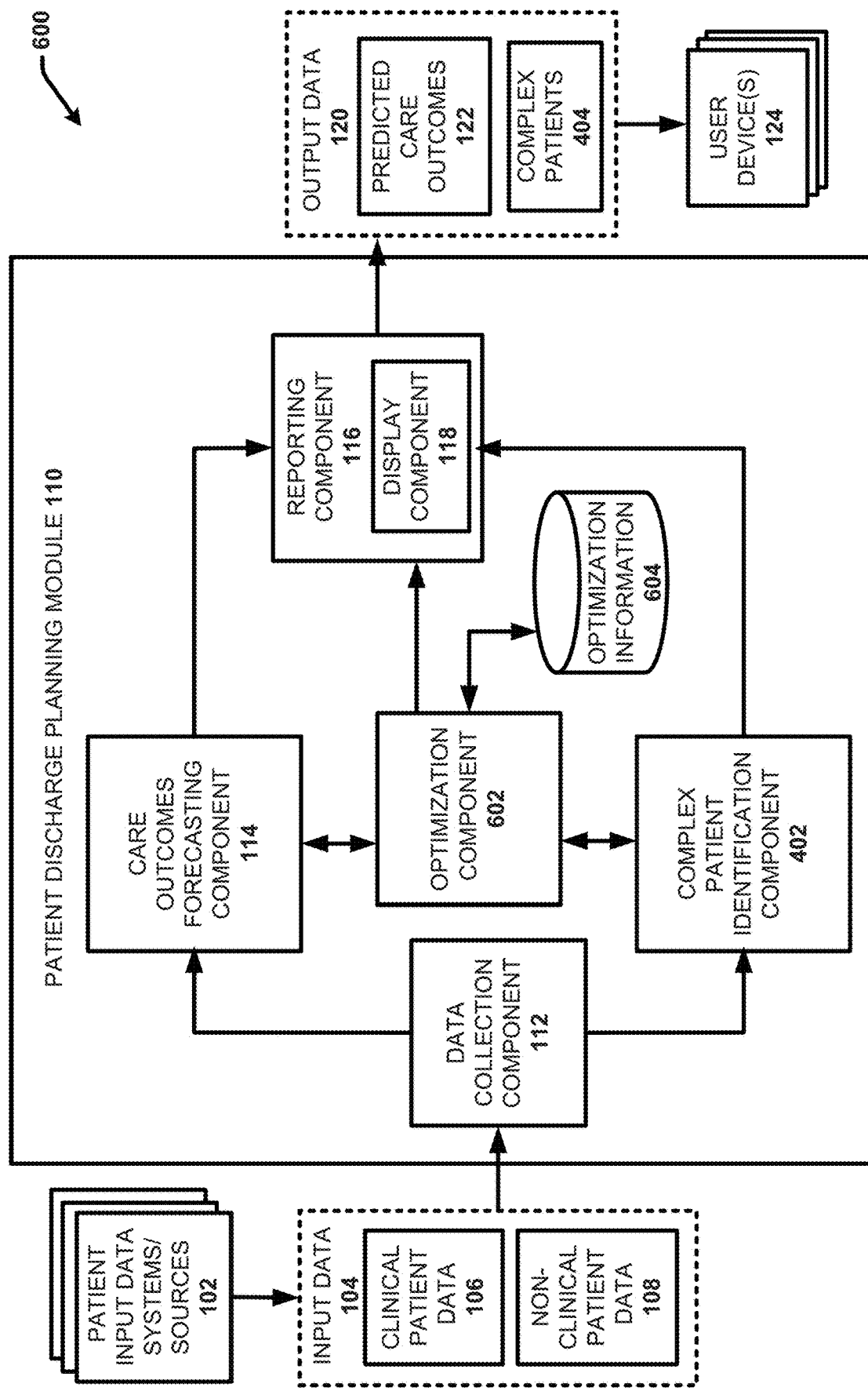
FIG. 6 illustrates a block diagram of another example, non-limiting system for forecasting patient discharge events and needs using machine learning analytics in accordance with one or more embodiments of the disclosed subject matter.

FIG. 6 illustrates a block diagram of another example, non-limiting system 600 for forecasting patient discharge events and needs using machine learning analytics in accordance with one or more embodiments of the disclosed subject matter. System 600 includes same or similar features as system 400 with the addition of optimization component 602 and optimization information 604 to the patient discharge planning module 110. Repetitive description of like elements employed in respective embodiments is omitted for sake of brevity.

In one or more embodiments, the disclosed care outcomes forecasting techniques can employ an ensemble machine learning approach that involves chaining and/or stacking of a plurality of different predictive models and employing the aggregated outputs of all the different models to converge on a final optimized prediction. With these embodiments, the respective forecasting models (e.g., the discharge destination foresting models 126, the LOS forecasting models 132, the readmission risk forecasting models 138 and/or the safety risk forecasting models 144) can include a plurality of different models respectively configured to forecast their corresponding patient care outcomes based on different combinations of clinical and/or non-clinical factors (e.g., different input parameters), using different weighting schemes for one or more of the input parameters, and/or using different types of machine learning algorithms/models. With these embodiments, the optimization component 602 can combine/aggregate and evaluate the outputs of the individual models to generate an optimized care outcome forecast. In accordance with these embodiments, the predicted care outcomes 122 can comprise optimized discharge destination forecasts, optimized discharge time/LOS forecasts 136, optimized readmission risk forecasts 142 and/or optimized safety risk forecasts 148). predictions. Information that controls how the optimization component 602 combines the aggregated care outcome predictions to generate the optimized care outcome forecasts can be defined in an optimization information 604 data store.

Figure 7:
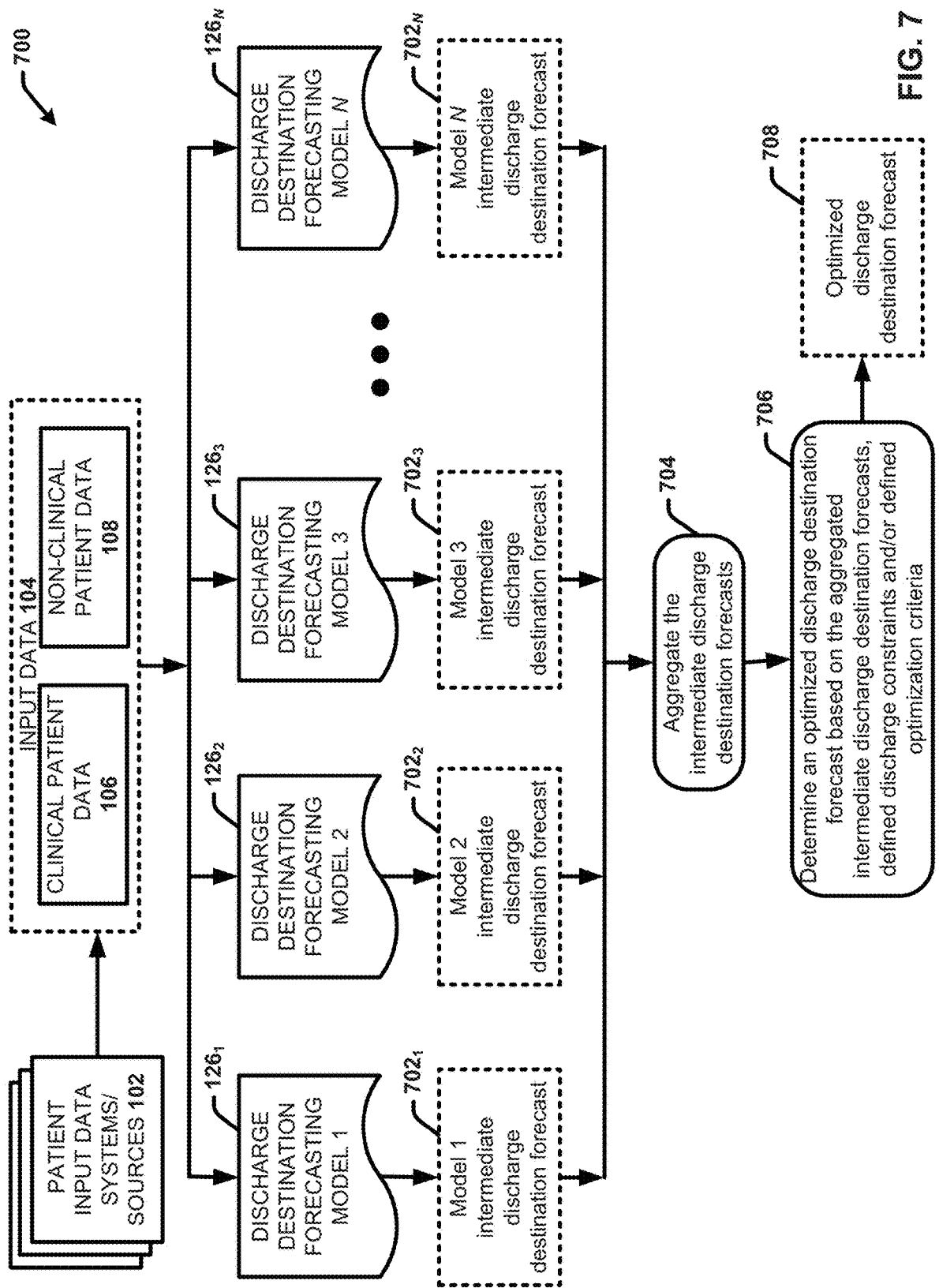
FIG. 7 presents a flow diagram illustrating an ensemble-based machine learning approach for forecasting patient discharge destinations in accordance with one or more embodiments of the disclosed subject matter.

In this regard, FIG. 7 presents a flow diagram 700 illustrating an ensemble-based machine learning approach for forecasting patient discharge destinations in accordance with one or more embodiments of the disclosed subject matter. Repetitive description of like elements employed in respective embodiments is omitted for sake of brevity.

With reference to FIG. 7 and FIG. 1B, in the embodiment shown, a plurality of different discharge destination forecasting machine learning models are used to generate intermediate discharge destination forecasts for currently admitted patients based on the input data 104. These different models are respectively identified as discharge destination forecasting model $126_1$, discharge destination forecasting model $126_2$, discharge destination forecasting model $126_3$, and discharge destination forecasting model $126_N$, (wherein N can represent any integer). The number of different discharge destination models can vary. The intermediate discharge destination forecasts determined/output by the respective models are identified as intermediate discharge destination forecast $702_1$, intermediate discharge destination forecast $702_2$, intermediate discharge destination forecast $702_3$, and so on up to intermediate discharge destination forecast $702_N$. Each (or in some implementations one or more) of the intermediate discharge destination forecasts $702_{1-N}$, can include one or more predicted discharged destinations/dispositions where a currently admitted patient may be discharged to, and in some implementations, placement probabilities indicating the predicted likelihood of the patient being admitted to the one or more discharge destinations/dispositions.

In some embodiments, the different discharge destination forecasting models can be trained/configured to process different sets of input parameters included in the input data 104. For example, the first discharge destination forecasting model $126_1$ can be trained/configured determine a first intermediate discharge destination forecast $702_1$ based on a first set of clinical and/or non-clinical factors, the second discharge destination forecasting model $126_2$ can be trained/configured determine a second intermediate discharge destination forecast $702_2$ based on a second set of clinical and/or non-clinical factors, the third discharge destination forecasting model $126_3$ can be trained/configured determine a third intermediate discharge destination forecast $702_3$ based on a third set of clinical and/or non-clinical factors, and so on. With these embodiments, the discharge destination forecasting component 128 (or the data collection component 112) can identify and extract the different sets of input parameters from the input data 104. The discharge destination forecasting component 128 can then apply the respective models to the specific input parameter sets they are respectively configured to process to generate the respective intermediate discharge destination forecasts.

The usage of different models respectively configured to make discharge predictions using different sets of input parameters enables a stacked machine learning approach, wherein the discharge destination forecasting component 128 can call and apply certain models based on the available data for a particular patient at current point in time when a discharge prediction is being made. For example, over the course of a patients' inpatient stay, new input data 104 can be received (e.g., care progression data 2018, case worker data 210, etc.) at different times. In addition, some input parameters values required by a particular model may not be received/provided for a patient (e.g., because the input parameter does not apply to the patient and/or is not included in the input data 104 collected for that patient). In this regard, in one or more embodiments, the discharge destination forecasting component 128 can evaluate all the input data 104 received for a patient up to a current point in time when a discharge disposition forecast is being made (e.g., by request, as scheduled, in response to a trigger event, etc.) to determine which discharge destination forecasting models can be applied based on whether the collective input data 104 includes all (or most) of the respective models' required input parameter values. Accordingly, the specific discharge destination models that are used for a particular patient at a given point in time will depend on the collective input data received, which can vary from patient to patient and vary as a function of time progression over the course of their inpatient stay. This approach can result in generating highly personalized discharge disposition forecasts that are tailored to a patient's individual case and needs at a current point in the inpatient stay.

In other implementations, the different discharge destination forecasting models $702_{1-N}$, can also (or alternatively) include two or more models respectively configured to process the same input parameter set, yet apply a different weighting scheme for the parameters. For example, one model can apply a weighting scheme that is biased (e.g., gives more weight to) toward clinical factors as opposed to non-clinical factors, while another model can apply a different weighting scheme that is biased toward non-clinical factors as opposed to clinical factors.

In another implementation, the different discharge destination forecasting models $702_{1-N}$, can also (or alternatively) include different types of machine learning models. For example, the different types of machine learning models can include but are not limited to: a nearest neighbor model, a naïve Bayes model, a decision tree model, a boosting model, a gradient boosting model, a linear regression model, a neural network model, a k-means clustering model, an association rules model, a q-learning model, a temporal difference model, a deep adversarial network model, or a combination thereof. The optimization component 602 can further combine/fuse the different output predictions in accordance with a defined weighting scheme to generate a final output prediction that balances the strengths and weaknesses of the different types of machine learning models.

In accordance with flow diagram 700, at 704 the optimization component 602 can aggregate the intermediate discharge destination forecasts. At 706, the optimization component 602 can further determine an optimized discharge destination forecast 708 for the patient based on the aggregated intermediate discharge destination forecasts, defined discharge constraints, and/or defined optimization criteria. In this regard, the defined optimization criteria can include information that controls how the optimization component 602 should combine the aggregated outputs to generate the generate the optimized discharge disposition forecast 708. For example, in some embodiments, the optimization criteria can define a weighting scheme for applying to the different model predications (e.g., give model 1 predictions X % weight, give model 2 predication Y % weight, etc.). With these embodiments, the optimization component 602 can combine the intermediate discharge destination forecasts based on the defined weighting scheme. In some implementations, the defined weighting scheme applied can be based on learned relevance and accuracy of the respective models for different patient groups (e.g., grouped by diagnosis, demographic factors, insurance factors, socioeconomic factors, etc.). In this regard, different weighting schemes for applying to the respective models can be defined for different patient groups (e.g., for patients included in subgroup A, give model 1 predictions X % weight, give model 2 predication Y % weight, for patients included in subgroup B, give model 1 predictions Y % weight, give model 2 predication Z % weight etc.). The criteria used to group the different patients into subgroups can vary (e.g., grouped by diagnosis, demographic factors, insurance factors, socioeconomic factors, etc.). With these implementations, the optimization component 602 can further apply the appropriate weighting scheme to the respective model outputs based on the specific patient group to which the patient being evaluated belongs. The optimization component 602 can also be configured to determine a discharge destination for a patient based on the number of models that converged on the same or a similar (e.g., with respect to the placement probabilities) result. For example, the optimization component 602 can select the top N (e.g., one, two, etc.) discharge destinations that were most frequently predicted by the collective. The optimization component 602 can also adjust the placement probability for a selected discharge destination based on the different probabilities determined for the same discharge destination by the different models (e.g., use the average of the different probabilities, or the like), as well as the different placement probabilities determined for other discharge destinations.

In some embodiments, the optimization component 602 can also employ defined constraints regarding where and when a patient can be discharged to facilitate determining the optimized discharge destination forecast 708 for a currently admitted patient. For example, the defined discharge constraints can include constraints regarding required care needs of the patient, financial constraints, insurance constraints, regulatory requirement constraints (e.g., defined service level agreements (SLAs)), family support constraints, resource constraints, known barriers to discharge, and the like. For example, in implementations in which the intermediate discharge destination forecasts $702_{1-N}$ include different forecasted destinations (e.g., one predicted discharge home, another predicted discharge to SNF, another predicted discharge to LTAC, etc.), the optimization component 602 can eliminate (e.g., rule out) a particular discharge destination based on a defined constraint associated with the patient that prevents the patient from going to that particular discharge destination. (e.g., patient cannot be discharged to disposition "ABC" because it is not covered by the patient's insurance and the patient cannot pay out of pocket). It should be appreciated the defined constraints can include criteria that was not accounted for in the discharge destination forecasting models applied. In various embodiments, the defined constraints can include constraints that are unique/personalized for the particular patient being evaluated.

In one or more additional embodiments in which the intermediate discharge destination forecasts $702_{1-N}$ include different forecasted discharge destination options and/or in which the optimization component 602 identifies several discharge destination options where the patient can be discharged (e.g., after applying the defined constraints and any known barriers to discharge), the optimization component 602 can further employ one or more optimization functions to select one or more of the discharge destination options to recommend for placing the patient. For example, the optimization component 602 can determine the most economically feasible option, the most convenient option (e.g., based on location factors, based on timing factors, etc.), the option that provides the highest level/quality of care, the option that best satisfies the patient's preferences (e.g., as included in the patient preference data 220), and the like. In this regard, the optimization component 602 can apply one or more defined optimization functions to facilitate selecting one or more discharge destinations from a group of possible discharge destination options to recommend. The one or more defined optimization function can be configured to satisfy and/or balance one or more defined optimization criterion, including but not limited to: minimize LOS, minimize discharge delay times, minimize costs, optimize patient flow, satisfy patient preferences, minimize recovery time, and minimize travel between required medical appointments.

The disclosed ensemble-based machine learning approach can also be used by the LOS forecasting component 134, the readmission risk forecasting component 140 and/or the safety risk forecasting component 146.

Figure 8:
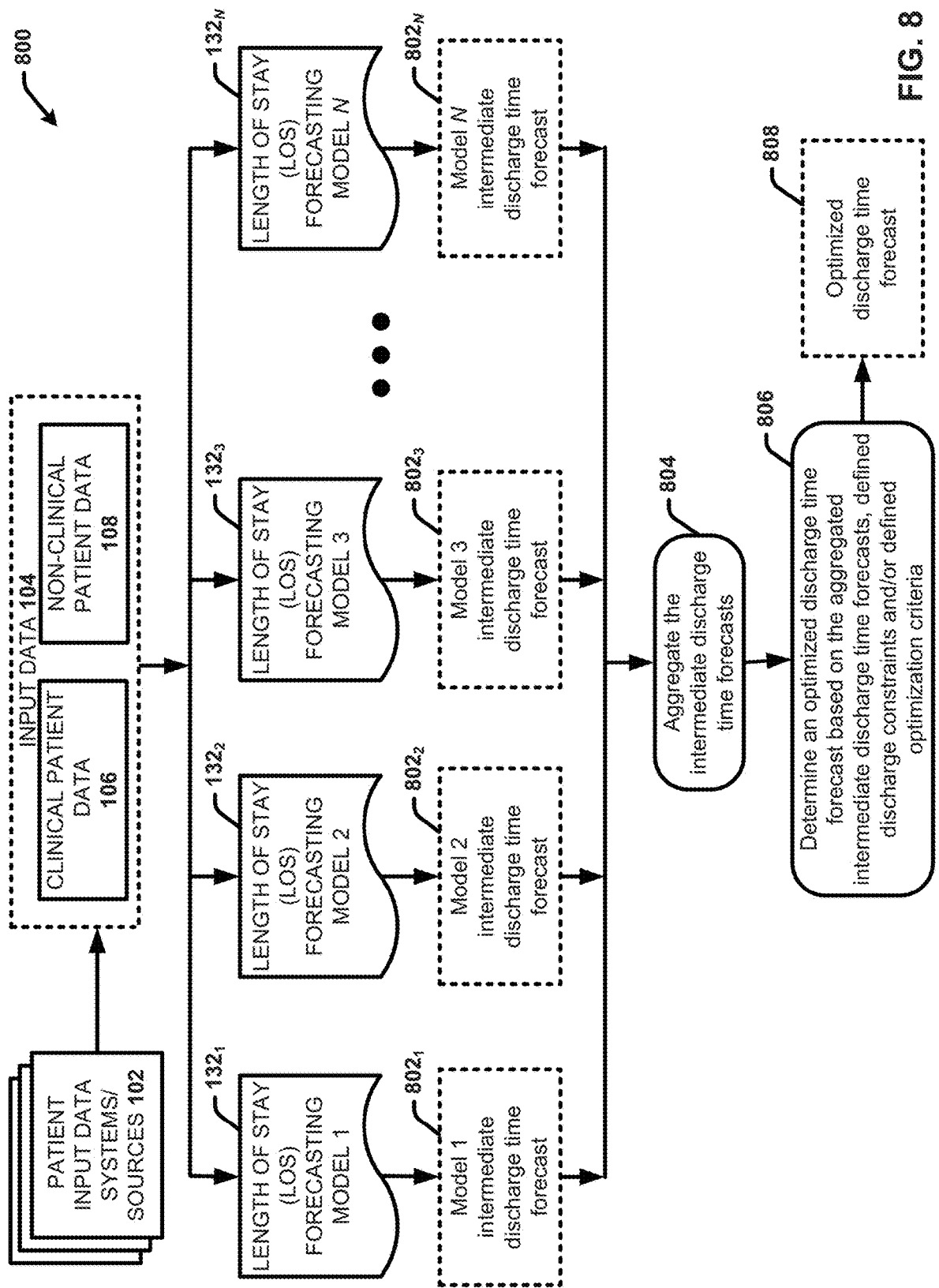
FIG. 8 presents a flow diagram illustrating an ensemble-based machine learning approach for forecasting patient discharge times in accordance with one or more embodiments of the disclosed subject matter.

For example, FIG. 8 presents a flow diagram 800 illustrating an ensemble-based machine learning approach for forecasting patient discharge times in accordance with one or more embodiments of the disclosed subject matter.

With reference to FIG. 8 and FIG. 1B, in the embodiment shown, a plurality of different LOS forecasting models are used to generate intermediate discharge time forecasts for currently admitted patients based on the input data 104. These different models are respectively identified as discharge time forecasting model $132_1$, discharge time forecasting model $132_2$, discharge time forecasting model $132_3$, and discharge time forecasting model $132_N$, (wherein N can represent any integer). The number of different LOS forecasting models can vary. The intermediate discharge time forecasts determined/output by the respective models are identified as intermediate discharge time forecast $802_1$, intermediate discharge time forecast $802_2$, intermediate discharge time forecast $802_3$, and so on up to intermediate discharge time forecast $802_N$. Each (or in some implementations one or more) of the intermediate discharge time forecasts $8021_{1-N}$, can include one or more predicted discharged times at which the patient is expected to be discharged and/or a predicted LOS. In some implementations in which a discharge time forecast includes two or more possible discharge times, the respective discharge times can also be associated with probabilities indicating the expected likelihood of the patient being discharged at the respective times.

In some embodiments, the different LOS forecasting models $132_{1-N}$ can be trained/configured to process different sets of input parameters included in the input data 104. For example, the first discharge time forecasting model $132_1$ can be trained/configured determine a first intermediate discharge time forecast $802_1$ based on a first set of clinical and/or non-clinical factors, the second discharge time forecasting model $132_2$ can be trained/configured determine a second intermediate discharge time forecast $802_2$ based on a second set of clinical and/or non-clinical factors, the third discharge time forecasting model $132_3$ can be trained/configured determine a third intermediate discharge time forecast $802_3$ based on a third set of clinical and/or non-clinical factors, and so on. With these embodiments, the LOS forecasting component 134 (or the data collection component 112) can identify and extract the different sets of input parameters from the input data 104 for feeding into the respective LOS forecasting models $132_{1-N}$ to generate the respective intermediate discharge destination forecasts. In this regard, as discussed with respect to the discharge destination forecasting models $126_{1-N}$, as new input parameters are collected for a patient over the course of the patient's stay, the LOS forecasting component 134 can selectively call and apply the appropriate models configured to account for the new input parameters at that time.

In other implementations, the different LOS forecasting models $802_{1-N}$, can also (or alternatively) include two or more models respectively configured to process the same input parameter set, yet apply a different weighting scheme for the parameters. In another implementation, the different discharge destination forecasting models $802_{1-N}$, can also (or alternatively) include different types of machine learning models. For example, the different types of machine learning models can include but are not limited to: a nearest neighbor model, a naïve Bayes model, a decision tree model, a boosting model, a gradient boosting model, a linear regression model, a neural network model, a k-means clustering model, an association rules model, a q-learning model, a temporal difference model, a deep adversarial network model, or a combination thereof. The optimization component 602 further combine/fuse the different output predictions in accordance with a defined weighting scheme to generate a final output prediction that balances the strengths and weaknesses of the different types of machine learning models.

In accordance with flow diagram 800, at 804 the optimization component 602 can aggregate the intermediate discharge time forecasts. At 806, the optimization component 602 can further determine an optimized discharge destination forecast 808 for the patient based on the aggregated intermediate discharge time forecasts, defined discharge constraints, and/or defined optimization criteria. In this regard, the defined optimization criteria can include information that controls how the optimization component 602 should combine the aggregated outputs to generate the generate the optimized discharge time forecast 808. For example, in some embodiments, the optimization criteria can define a weighting scheme for applying to the different model predications (e.g., give model 1 predictions X % weight, give model 2 predication Y % weight, etc.). With these embodiments, the optimization component 602 can combine the intermediate discharge time forecasts based on the defined weighting scheme. In some implementations, the defined weighting scheme applied can be based on learned relevance and accuracy of the respective models for different patient groups. The criteria used to group the different patients into subgroups can vary (e.g., grouped by diagnosis, demographic factors, insurance factors, socioeconomic factors, etc.). With these implementations, the optimization component 602 can further apply the appropriate weighting scheme to the respective model outputs based on the specific patient group to which the patient being evaluated belongs. The optimization component 602 can also be configured to determine an optimal discharge time forecast for a patient based on the number of models that converged on the same or a similar result. In another embodiment, the optimization component 602 can determine an optimal discharge time forecast by taking the mean or median of the different discharge times and/or LOS values generated by the respective models.

In some embodiments, the optimization component 602 can also employ defined constraints regarding where and when a patient can be discharged to facilitate determining the optimized discharge time forecast 808 for a currently admitted patient. For example, the defined discharge constraints can include constraints regarding required care needs of the patient, financial constraints, insurance constraints, regulatory requirement constraints (e.g., defined service level agreements (SLAs)), family support constraints, resource constraints, known barriers to discharge, and the like. For example, a patient's insurance policy can require a patient stay a minimum of N days before discharge to a SNF to be covered. According to this example, the optimization component 602 can eliminate any LOS predictions that are less than N days if the patient has a predicted discharge destination to a SNF with a high probability (e.g., relative to a defined threshold, such as 90% or greater) and the patient is unable or unwilling to pay for the SNF services out of pocket. In various embodiments, the defined constraints can include constraints that are unique/personalized for the particular patient being evaluated.

Figure 9:
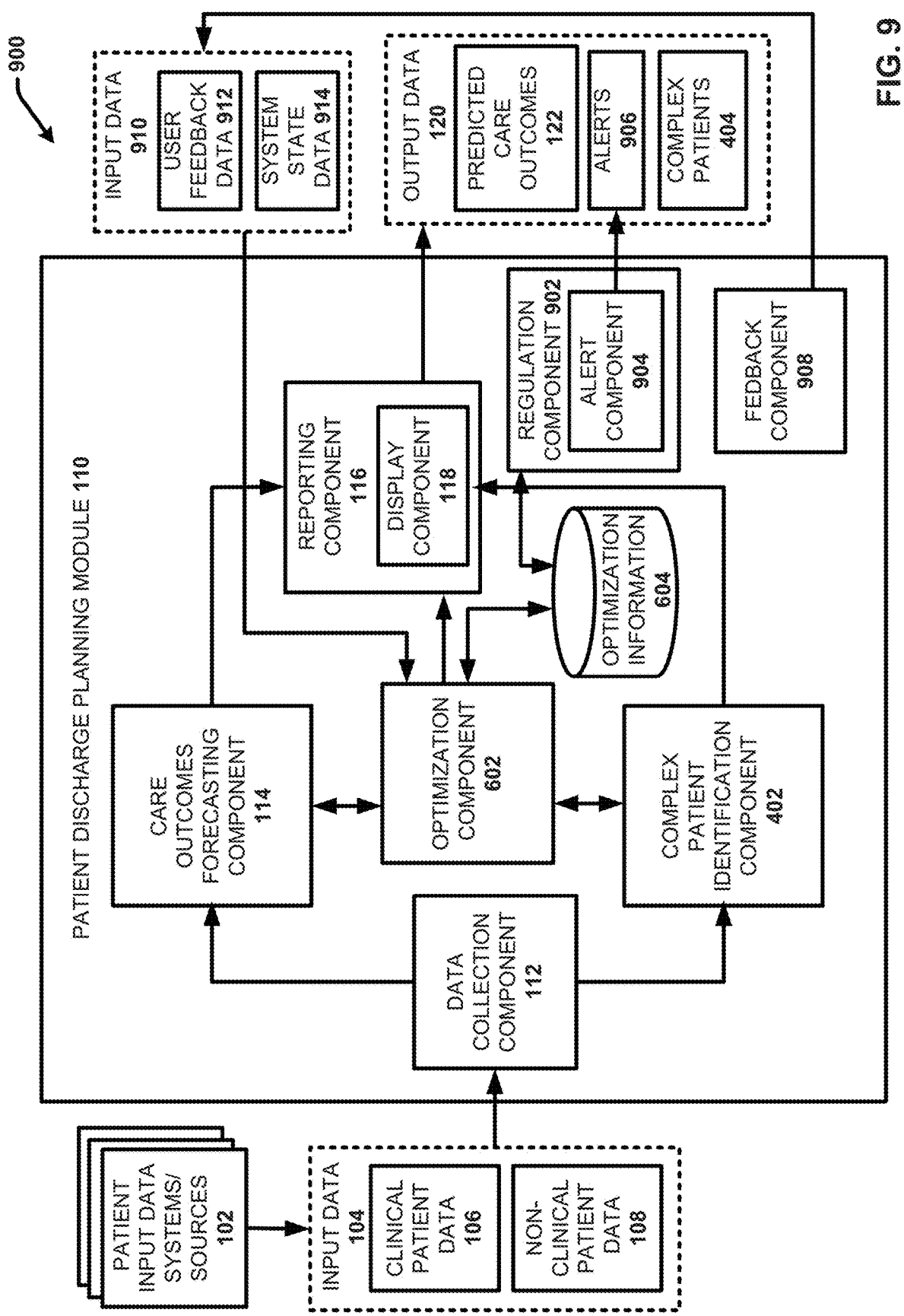
FIG. 9 illustrates a block diagram of another example, non-limiting system for forecasting patient discharge events and needs using machine learning analytics in accordance with one or more embodiments of the disclosed subject matter.

FIG. 9 illustrates a block diagram of another example, non-limiting system 900 for forecasting patient discharge events and needs using machine learning analytics in accordance with one or more embodiments of the disclosed subject matter. System 900 includes same or similar features and functionalities as system 600 with the addition of regulation component 902, and feedback component 908 to the patient discharge planning module 110. System 900 also includes the addition of alerts 906 to the output data 120 and input data 910. Although not shown, it should be appreciated that system 900 can also include one or more user devices 122 for receiving and/or rendering the output data 120 and/or facilitating user interaction with the patient discharge planning module 110. Repetitive description of like elements employed in respective embodiments is omitted for sake of brevity.

In some embodiments, the optimization component 602 can receive additional input data 910 including user feedback data 912 and/or system state data 914 to facilitate determining optimized discharge destination forecasts and/or optimized discharge time forecasts. The user feedback data 912 can include information relevant to a patient's discharge provided by one or more individuals involved in the patient's care (e.g., a care provider, a case worker, a family member, a friend, the patient, etc.). For example, the user feedback data 912 can include user reported information identifying barriers to discharge including clinical and non-clinical tasks to be performed and/or scheduled prior to discharge, during discharged and/or following discharge (e.g., arranging dialysis, scheduling a consult, arranging/scheduling transportation, managing dietary requirements, setting up medication delivery, etc.). The user feedback data 912 can also include information regarding completed tasks and/or discharge milestones. The user feedback data 912 can include contextual information regarding arranging and performing check out of the patient from the hospital, including information regarding who will be accompanying the patient away from the hospital, when they will be arriving, how they will be transporting the patient, and the like.

In various embodiments, the feedback component 908 can facilitate receiving user feedback data 912 regarding barriers to discharge (e.g., tasks to be performed), tasks completed (e.g., milestones), tasks scheduled and the like. For example, in some embodiments, the feedback component 908 can include and/or be associated with a patient discharge planning application that facilitates planning a patient's discharge, including managing and coordinating relevant tasks and activities associated a patient's discharge. With these embodiments, the user feedback data 912 can include information received via the patient discharge planning application.

Figure 10:
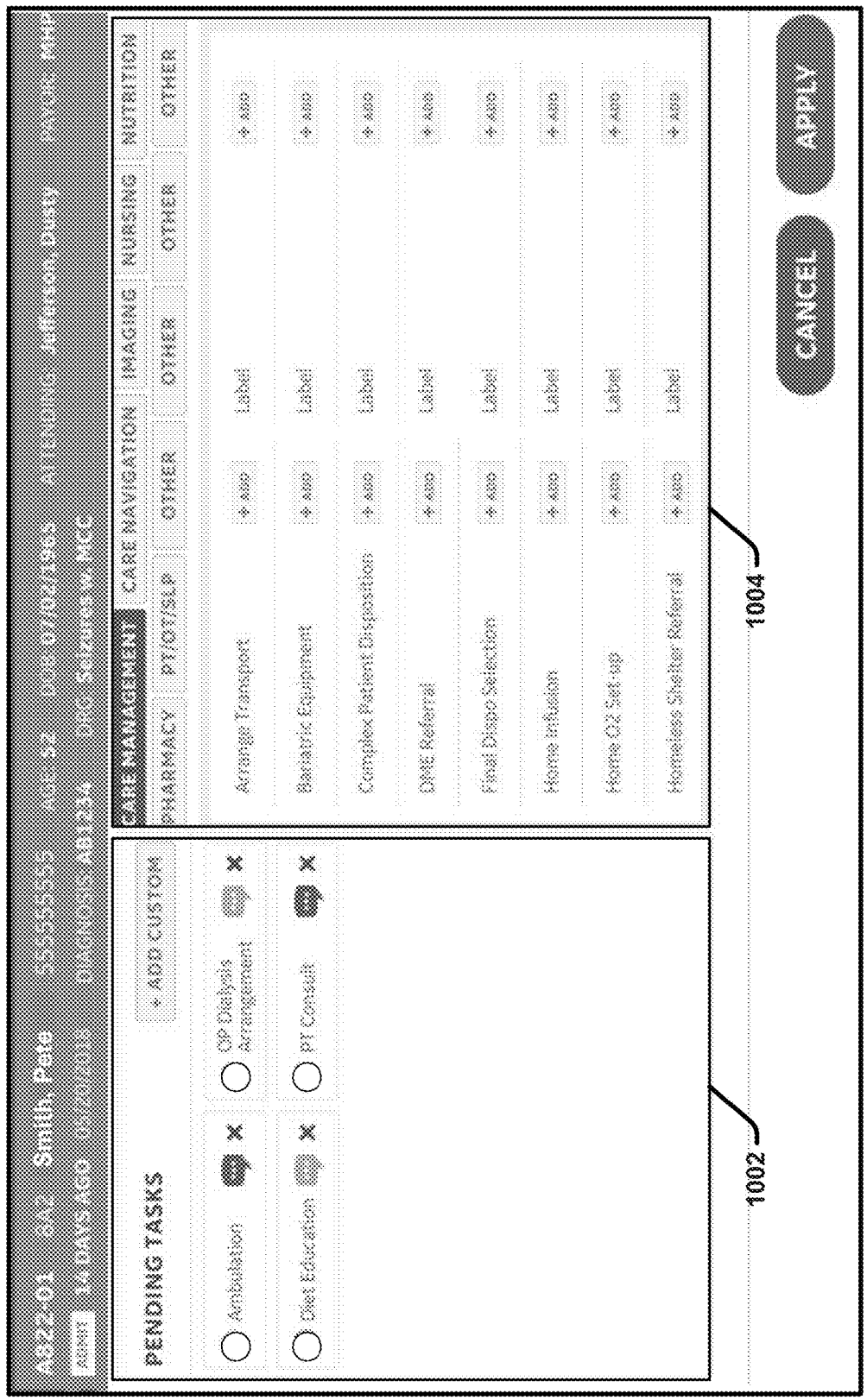
FIG. 10 presents an example graphical user interface (GUI) that facilitates planning and coordinating patient discharge events in accordance with one or more embodiments of the disclosed subject matter.

For example, FIG. 10 presents an example GUI 1000 that facilitates receiving user feedback data 912 regarding patient discharge barriers and milestones in accordance with one or more embodiments of the disclosed subject matter. In various embodiments, GUI 1000 is an example GUI that can be generated and/or provided by the feedback component 908 and/or the display component 118 to facilitate coordinating patient care and capturing user feedback (e.g., user feedback data 912) regarding patient care needs, barriers to discharge, and the like.

In accordance with this example implementation, the GUI 1000 can include a pending tasks element management element 1004 that allows a user (e.g., a case worker, a care provider or the like) to select and add tasks that need to be (or are preferred to be) completed for the patient to facilitate smooth discharge and/or to record information regarding completed tasks and/or milestones. These can include tasks to be completed before discharge, as well as tasks to be completed after discharge and/or in association with placing the patient at a particular discharge destination. For example, in the embodiment shown, the tasks and/or milestones are organized into different categories in selectable tabs, including care management, care navigation, imaging, nursing, nutrition, pharmacy, and PTO/OT/SLP. In this example, the care management tab is selected and a list of know tasks that fall into this category are displayed. In some implementations, the specific task options available for selection can be pre-populated based on the patient's forecasted discharge disposition and/or other criteria (e.g., diagnosis, medical history, clinical orders, etc.). The user can further select tasks to add, provide notes and/or comments regarding the selected tasks and the like. All selected and pending tasks for the patient are shown on the left side of the GUI in the pending tasks window 1002. The pending tasks window 1002 can also allow the user to add custom tasks and add notes regarding the pending tasks, mark tasks as completed, remove tasks and the like.

Figure 11:
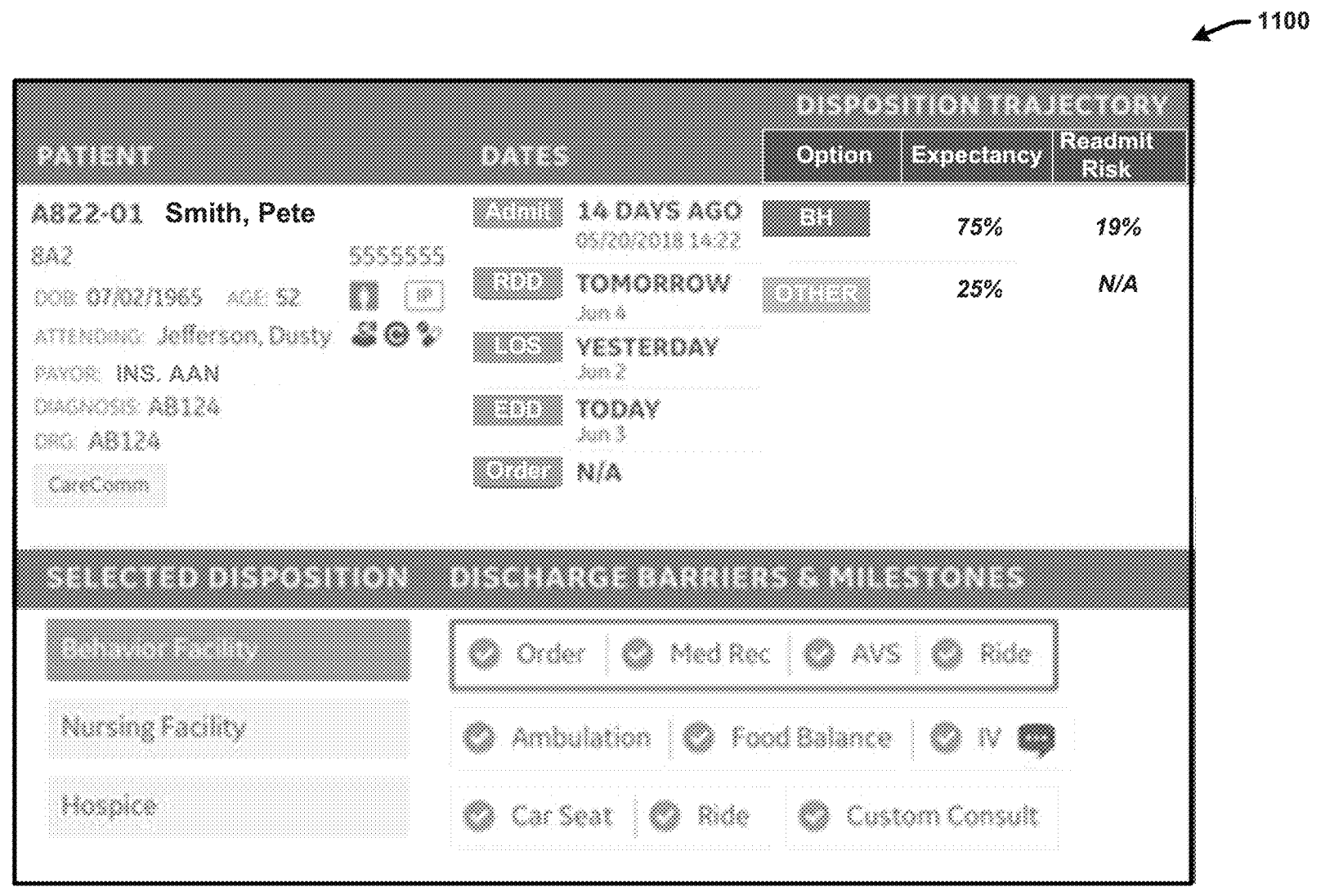

FIG. 11 presents another example GUI 1100 that facilitates planning and coordinating patient discharge events in accordance with one or more embodiments of the disclosed subject matter. In various embodiments, GUI 1100 is another example GUI that can be generated and/or provided by the feedback component 908 and/or the display component 118 to facilitate coordinating patient care and capturing user feedback (e.g., user feedback data 912) regarding patient care needs, barriers to discharge, and the like.

In accordance with this example implementation, the top portion of the GUI 1100 can display information relevant to a selected patient and their forecasted disposition trajectory. For example, top portion of the GUI 1100 includes general patient demographic information, insurance information, physician information, diagnosis in formation, and the like. The top portion of the GUI 1100 also includes information regarding relevant dates, including the admission date, the required discharge data (RDD), the predicted LOS, the expected discharge date (EDD), and pending order dates. The top portion of the GUI 1100 also includes predicted discharge destination options, percent expectancy of discharge to the predicted discharge options, and predicted readmission risk associated with discharge to the respective discharge destinations. In this example, the primary predicted discharge destination is a behavior facility (BH). Other discharge destinations options are not explicitly identified and are grouped together generally. In some implementations, selection of the "other" GUI element can result in presenting information regarding other possible discharge destination options.

The bottom portion of the GUI 1100 includes information regarding known discharge barriers and milestones for a selected discharge disposition. In this example, the behavior facility discharge disposition is selected, and discharge barriers and milestones associated with discharge of the patient to the behavior facility are shown on the right. In various embodiments, information identifying the discharge barriers and milestones displayed in GUI 1100 can be received as user feedback data 912 (e.g., via GUI 1000).

With reference again to FIG. 9, the system state data 914 can include dynamic, real-time information regarding variable conditions associated with the state of the inpatient facility (e.g., hospital) where patients are being discharged from, as well as the state of the discharge destinations where patients are being discharged too, that can influence when and where the patients are discharged. For example, the system state data 914 can include real-time information regarding the operating conditions/contexts of the hospital that vary and can influence when and where a patient is discharged, including information regarding patient flow, bed availability, wait times for beds, and availability of resources (e.g., availability of care providers to assist patients, availability of medical supplies/equipment, availability of transportation services, etc.) and the like. The system state data 914 can also include information regarding the operating conditions/contexts of the respective discharge facilities where patients may be discharged, including information regarding bed availability and demand (e.g., wait times), availability of resources at the respective discharge facilities (e.g., patient needs "xyz" resources at the discharge facility upon arrival but these aren't available, aren't working, have long wait times, etc.) and the like. The system state data 914 can also include real-time information regarding insurance authorization processing, including whether an authorization request is pending, expected time to approval, and the like.

In this regard, in some embodiments, the optimization component 602 can further facilitate determining optimized discharge destinations forecasts, recommending preferred discharged destinations (e.g., when more than one discharge destination can provide the level and type of care a patient requires) and/or determining optimized discharge time forecasts based on the user feedback data 912 and/or the system state data 914. For example, the optimization component 602 can employ information regarding barriers to discharge reported in the user feedback data 912 to identify and select one or more discharge dispositions that account for the barriers (e.g., discharge dispositions that are possible in view of the barriers and/or that minimize or eliminate barriers), and/or to adjust the placement probabilities associated with one or more possible discharge dispositions based on the barriers. The optimization component 602 can also employ information regarding bed availability, wait times, availability of resources, discharge check out arrangements, insurance authorization processing and the like, included in received system state data 914 to identify and select one or more discharge dispositions that account for the factors and/or to adjust the placement probabilities associated with one or more possible discharge dispositions based on the barriers. For example, even once a patient is ready for discharge, it could take days for an insurance provider to review a patient's medical record to authorize discharged to a post-acute care facility. By the time the process is finished, a bed may not be available in the facility of the patient's choice the discharge. In accordance with this example, the optimization component 602 can employ real-time information included in the system state data 914 regarding bed availability at discharge destination options and expected time to receiving insurance authorization for placement to better predict where a patient will be discharged.

The optimization component 602 can similarly adjust the predicted discharge time forecast based on the received user feedback data 912 regarding barriers to discharge and/or completed milestones (e.g., removed barriers), and system state data 914 regarding bed availability, availability of resources, insurance authorization processes, and the like. For example, if there is something preventing a patient from being discharged at a certain time or getting to a forecasted discharge destination (e.g., a reported barrier, unavailability of beds/resources, an insurance processing delay, etc.), the LOS optimization can increase the predicted discharge time accordingly. In some embodiments, the optimization component 602 can facilitate determining patient discharge times based on the discharge destinations predicted for the respective patients and constraints reported in the user feedback data 912 and the system state data 914 associated with placing the respective patients at the discharge destinations. For example, assume the discharge destination forecasting component 128 and/or the optimization component 602 determines a discharge destination where a patient is likely to be discharged too (e.g., with a placement probability exceeding a threshold probability). Based on this expected discharge destination, the optimization component 602 can identify information included in the user feedback data 912 and/or the system state data 914 that influences when the patient can be discharged to the discharge destination and determine the expected discharge time based in part on these constraints.

In the embodiment shown, the patient discharge planning module 110 can further include a regulation component 902 to facilitate regulating the patient discharge process in accordance with defined rules, requirements and/or expectations. For example, in some implementations, the optimization information 604 can define various rules and requirements that control or influence when and where a patient is discharged. For instance, these rules and requirements can relate to patient care requirements (e.g., regarding where a patient can be discharged, regarding tasks to be completed before discharge, etc.), discharge protocol requirements, insurance policy requirements (e.g., regarding authorizations, regarding minimum and maximum LOS, etc.), SLA requirements (e.g., regarding minimum and maximum LOS, regarding discharge delays, regarding level/type of care provided, etc.), and the like.

In some embodiments, the regulation component 902 can identify violations and/or potential violations to the defined rules and requirements (as defined in the optimization information 604) based on the predicted discharge destinations and/or predicted discharge times, and in some implementations the user feedback data 912 and the system state data 914. The alert component 904 can further generate and provide alerts 906 regarding identified violations and/or potential violations. For example, the regulation component 902 can determine whether placing a patient at a predicted discharge destination violates a level of care requirement, an SLA requirement, an insurance policy, or the like. In another example, the regulation component 902 can determine whether a forecasted discharge time violates one or more rules or requirements defined in the optimization information 604. For example, the regulation component 902 can determine whether a predicted discharge time violates a minimum or maximum LOS requirement for the patient (e.g., defined by SLAs, defined by an insurance policy of the patient, etc.). In another example, the regulation component 902 can determine whether a barrier exists (e.g., reported in the user feedback data 912, and/or included in the system stat data 914 or the input data 104) that inhibits or prevents placing a patient at a forecasted discharge destination and/or that inhibits or prevents placing the patient at the forecasted discharge destination at the forecasted discharge time.

In some implementations, the regulation component 902 can also determine required tasks and/or events that need to occur before a patient can be discharged based on the predicted discharge destination (or destinations) determined for the patient. For example, based on forecasting that a patient will likely (e.g., relative to a threshold placement probability) be discharged to a specific discharge destination, the regulation component 902 can determine one or more uncompleted tasks that need to be performed before the patient can be discharged to that particular discharge destination (e.g., ordering consultations, receiving insurance authorization, arranging oxygen transport, etc.). The alert component 904 can further generate and provide alerts 906 regarding the identified required tasks.

For example, FIG. 12 presents an example visualization 1200 reporting identified patient discharge barriers and associated alerts in accordance with one or more embodiments of the disclosed subject matter. Visualization 1200 provides another example display that can be generated by the display component 118 based on the output data 120 as generated/determined using the techniques described herein. In the embodiment shown, the visualization 1200 identifies three currently admitted patients and general information about the respective patients, including their MRN number, current medical department and unit, and insurance provider. The visualization also includes information regarding the patients' respective admission dates, expected or current LOS, and EDD. Tasks relevant to the patients' discharge are further identified via symbols. In some implementations, these tasks can include required tasks determined by the regulation component 902. The far-right side of the visualization further includes information regarding the patients' discharge status, transfer date and transfer time. In the embodiment shown, if a patients' discharge status is confirmed but barriers exist that prevent discharge (e.g., determined by the regulation component 902), a notification symbol can be displayed (e.g., generated by the alert component 906), as exemplified with the first patient, L.MCA.

Figure 13:
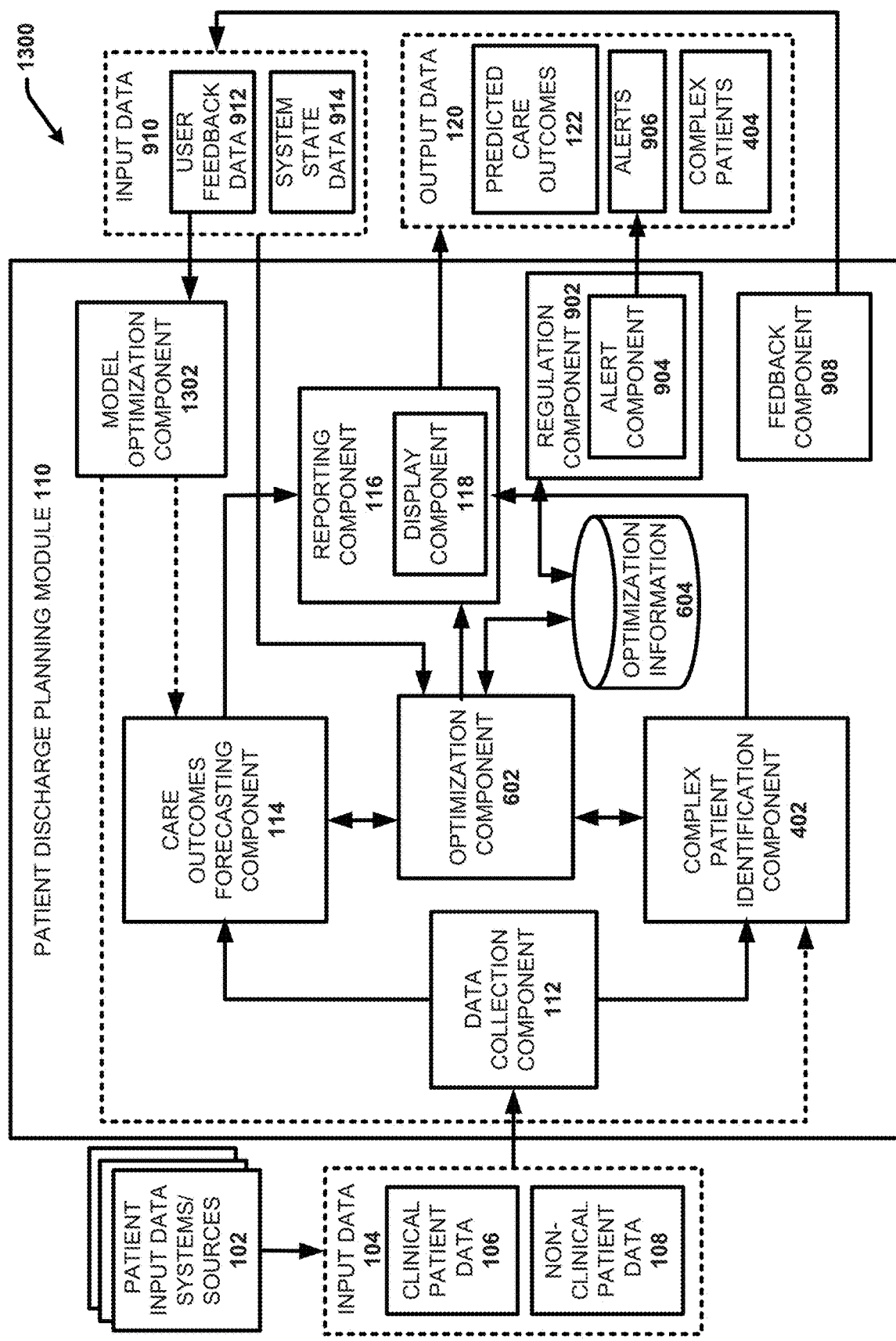
FIG. 13 illustrates a block diagram of another example, non-limiting system for forecasting patient discharge events and needs using machine learning analytics in accordance with one or more embodiments of the disclosed subject matter.

FIG. 13 illustrates a block diagram of another example, non-limiting system 1220 for forecasting patient discharge events and needs using machine learning analytics in accordance with one or more embodiments of the disclosed subject matter. System 1220 includes same or similar features and functionalities as system 900 with the addition of model optimization component 1222. Repetitive description of like elements employed in respective embodiments is omitted for sake of brevity.

In various embodiments, the one or more discharge destination forecasting models 126 and/or the one or more LOS forecasting models 132 can continuously learn and update over time based on new correlations observed between patient discharge destinations and time and the various parameters included in the input data 104 and the input data 910. With these embodiments, the model optimization component 1222 can facilitate training and updating the one or more discharge destination forecasting models 126 and/or the one or more LOS forecasting models 132 over time. For example, in some implementations, the model optimization component 1222 can feed user feedback data 912 regarding identified barriers (e.g., with status tracking), milestones, and associated comments, back into the discharge destination forecasting models 126 and the LOS forecasting models 132 to improve their accuracy. In this regard, the model optimization component 1222 can essentially facilitate a closed loop system where the feedback application also produces data used to improve the accuracy of the discharge destination forecasts and discharge time forecasts.

Figure 14:
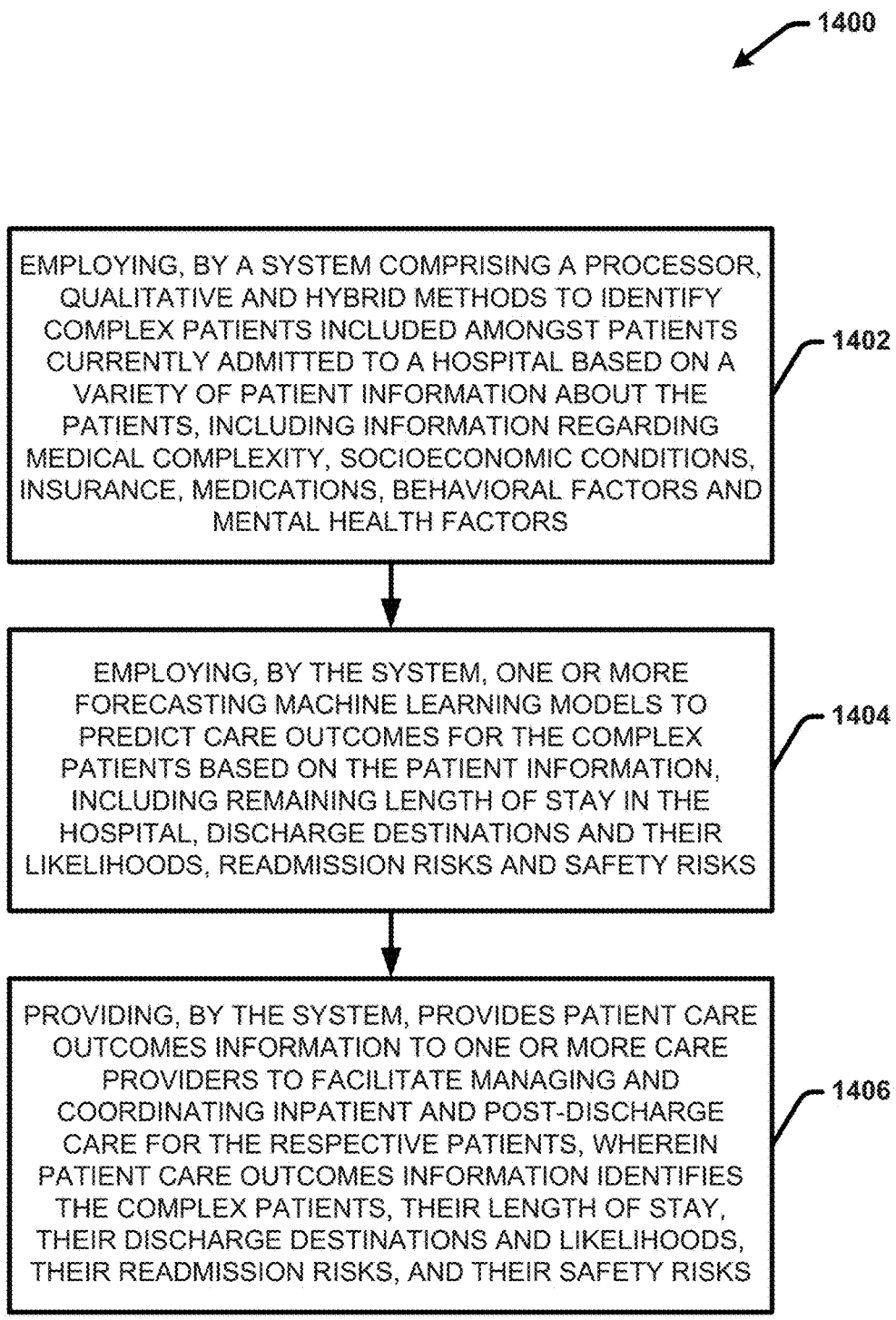
FIG. 14 illustrates an example, high-level flow diagram of a computer-implemented process for forecasting patient discharge events and needs using machine learning analytics in accordance with one or more embodiments of the disclosed subject matter.

FIG. 14 illustrates another example, high-level flow diagram of a computer-implemented process 1400 for forecasting patient discharge events and needs using machine learning analytics in accordance with one or more embodiments of the disclosed subject matter. Repetitive description of like elements employed in other embodiments described herein is omitted for sake of brevity.

At 1402, a system operatively coupled to a processor (e.g., system 100, system 400, system 600, system 900, system 1200 or the like), employs qualitative and hybrid methods to identify complex patients (e.g., using complex patient identification component 402) included amongst patients currently admitted to a hospital based on a variety of patient information about the patients (e.g., included in input data 104), including information regarding medical complexity, socioeconomic conditions, insurance, medications, behavioral factors and mental health factors. At 1404, the system employs one or more forecasting machine learning models to predict care outcomes for the complex patients based on the patient information (e.g., using care outcomes forecasting component 1414), including remaining length of stay in the hospital, discharge destinations and their likelihoods, readmission risks and safety risks. At 1406, the system provides patient care outcomes information (e.g., predicted care outcomes 122) to one or more care providers to facilitate managing and coordinating inpatient and post-discharge care for the respective patients, wherein patient care outcomes (e.g., via reporting component 116).

Figure 15:
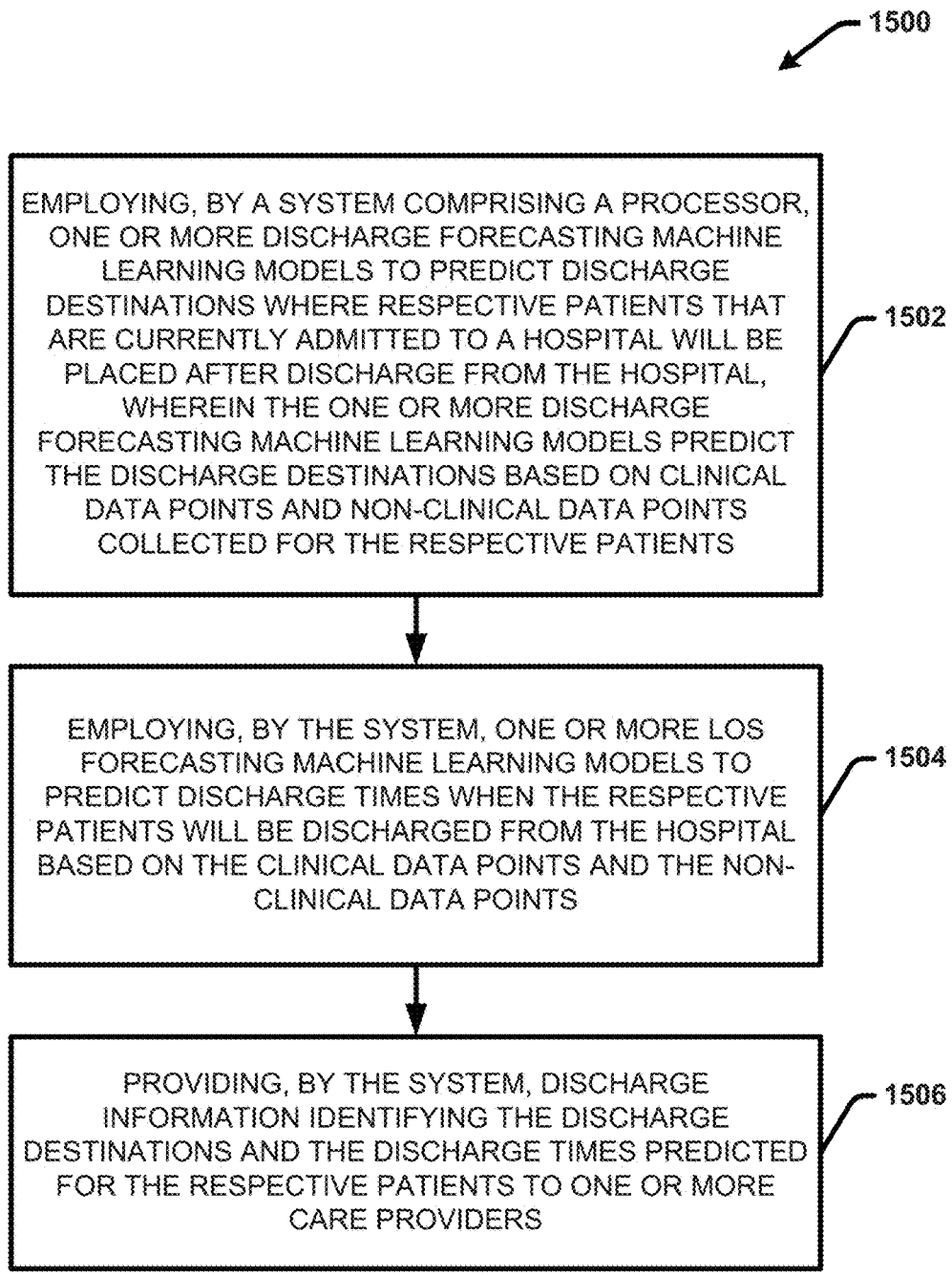
FIG. 15 illustrates another example, high-level flow diagram of another computer-implemented process for forecasting patient discharge events and needs using machine learning analytics in accordance with one or more embodiments of the disclosed subject matter.

FIG. 15 illustrates another example, high-level flow diagram of another computer-implemented process 1500 for forecasting patient discharge events and needs using machine learning analytics in accordance with one or more embodiments of the disclosed subject matter. Repetitive description of like elements employed in other embodiments described herein is omitted for sake of brevity.

At 1502, a system operatively coupled to a processor (e.g., system 100, system 400, system 600, system 900, system 1200 or the like), employs one or more discharge forecasting machine learning models (e.g., discharge forecasting models 126) to predict discharge destinations where respective patients that are currently admitted to a hospital will be placed after discharge from the hospital (e.g., using discharge destination forecasting component 128), wherein the one or more discharge forecasting machine learning models predict the discharge destinations based on clinical data points (e.g., clinical patient data 106) and non-clinical data points (e.g., non-clinical patient data 108) collected for the respective patients. At 1504, the system employs one or more LOS forecasting machine learning models (e.g., LOS forecasting model 122) to predict discharge times when the respective patients will be discharged from the hospital based on the clinical data points and the non-clinical data points (e.g., using LOS forecasting component 134). At 1506, the system provides discharge information identifying the discharge destinations predicted for the respective patients to one or more care providers to facilitate managing and coordinating inpatient and post-discharge care for the respective patients (e.g., via reporting component 116).

Figure 16:
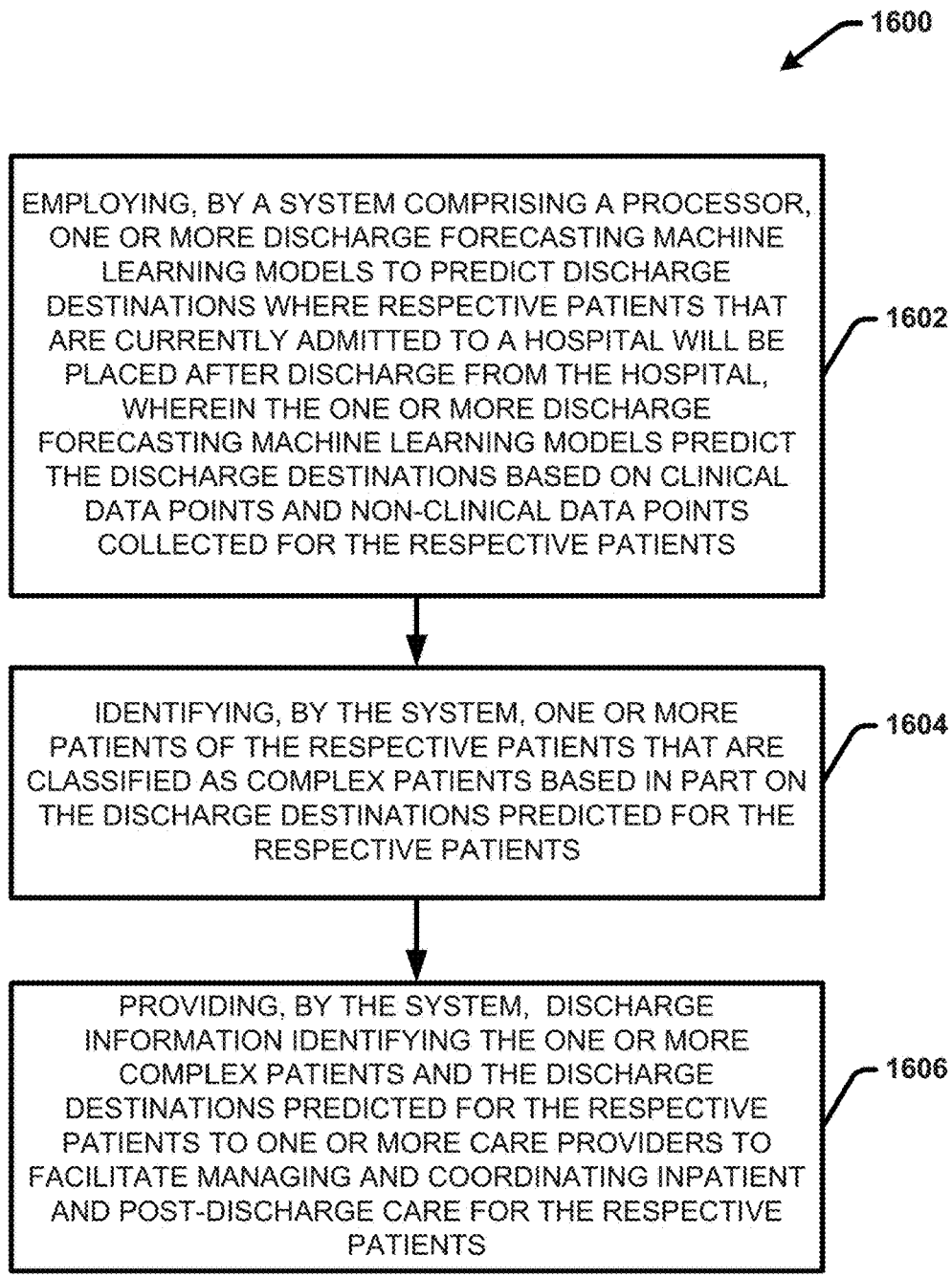
FIG. 16 illustrates another example, high-level flow diagram of another computer-implemented process for forecasting patient discharge events and needs using machine learning analytics in accordance with one or more embodiments of the disclosed subject matter.

FIG. 16 illustrates another example, high-level flow diagram of another computer-implemented process 1600 for forecasting patient discharge events and needs using machine learning analytics in accordance with one or more embodiments of the disclosed subject matter. Repetitive description of like elements employed in other embodiments described herein is omitted for sake of brevity.

At 1602, a system operatively coupled to a processor (e.g., system 400, system 600, system 900, system 1200 or the like), employs one or more discharge forecasting machine learning models (e.g., discharge forecasting models 126) to predict discharge destinations where respective patients that are currently admitted to a hospital will be placed after discharge from the hospital (e.g., using discharge destination forecasting component 128), wherein the one or more discharge forecasting machine learning models predict the discharge destinations based on clinical data points (e.g., clinical patient data 106) and non-clinical data points (e.g., non-clinical patient data 108) collected for the respective patients. At 1604, the system identifies one or more patients of the respective patients that are classified as complex patients based in part on the discharge destinations predicted for the respective patients (e.g., using complex patient identification component 402). At 1606, the system provides discharge information identifying the one or more complex patients (e.g., complex patients data 404) and the discharge destinations predicted for the respective patients to one or more care providers to facilitate managing and coordinating inpatient and post-discharge care for the respective patients (e.g., via reporting component 116).

Example Operating Environment

One or more embodiments can be a system, a method, and/or a computer program product at any possible technical detail level of integration. The computer program product can include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It can be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession may, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In connection with FIG. 17, the systems and processes described below can be embodied within hardware, such as a single integrated circuit (IC) chip, multiple ICs, an application specific integrated circuit (ASIC), or the like. Further, the order in which some or all of the process blocks appear in each process should not be deemed limiting. Rather, it should be understood that some of the process blocks can be executed in a variety of orders, not all of which can be explicitly illustrated herein.

Figure 17:
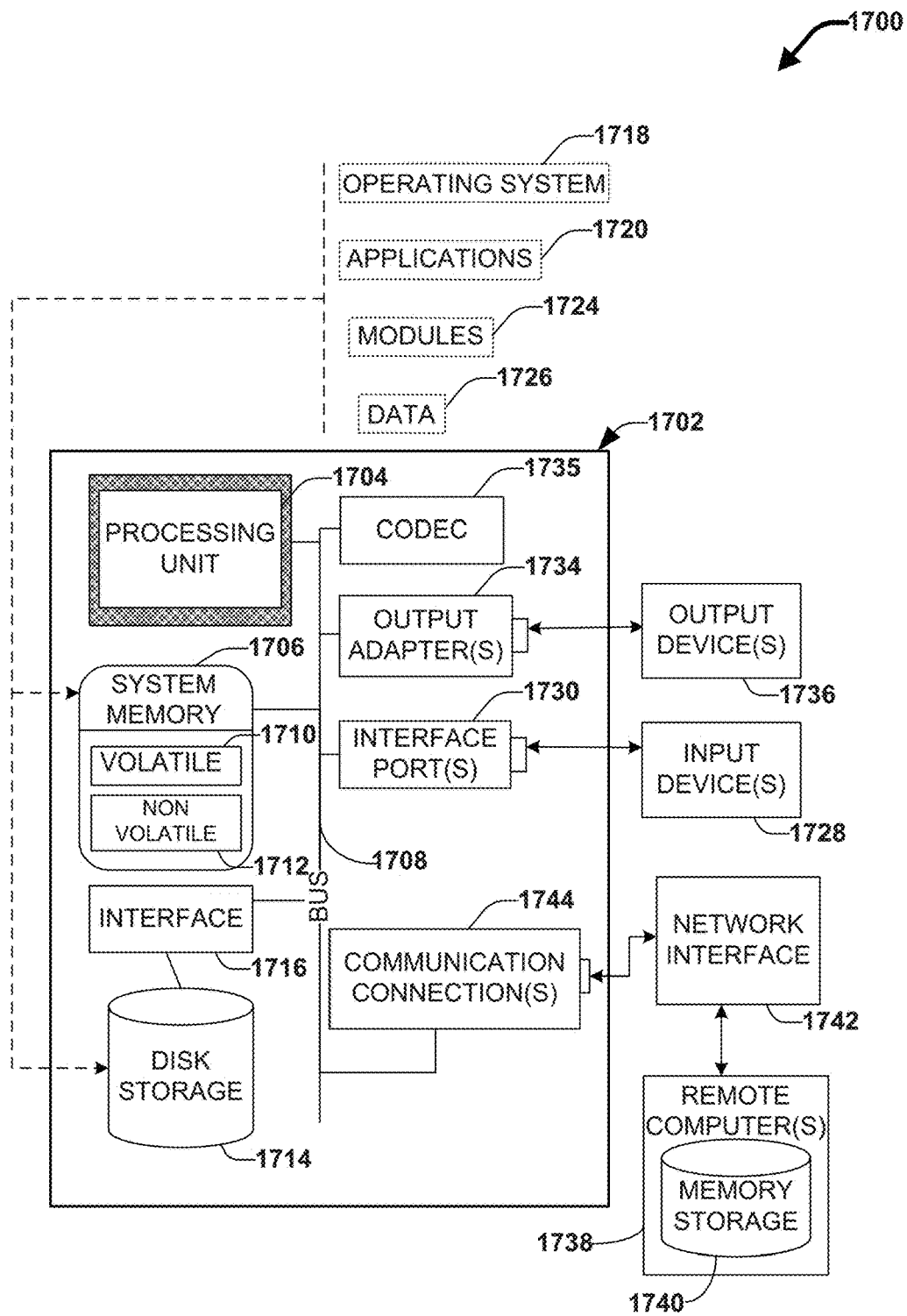
FIG. 17 illustrates a block diagram of an example, non-limiting operating environment in which one or more embodiments described herein can be facilitated.

With reference to FIG. 17, an example environment 1700 for implementing various aspects of the claimed subject matter includes a computer 1702. The computer 1702 includes a processing unit 1704, a system memory 1706, a codec 1735, and a system bus 1708. The system bus 1708 couples system components including, but not limited to, the system memory 1706 to the processing unit 1704. The processing unit 1704 can be any of various available processors. Dual microprocessors and other multiprocessor architectures also can be employed as the processing unit 1704.

The system bus 1708 can be any of several types of bus structure(s) including the memory bus or memory controller, a peripheral bus or external bus, or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1394), and Small Computer Systems Interface (SCSI).

The system memory 1706 includes volatile memory 1710 and non-volatile memory 1712, which can employ one or more of the disclosed memory architectures, in various embodiments. The basic input/output system (BIOS), containing the basic routines to transfer information between elements within the computer 1702, such as during start-up, is stored in non-volatile memory 1712. In addition, according to present innovations, codec 1735 can include at least one of an encoder or decoder, wherein the at least one of an encoder or decoder can consist of hardware, software, or a combination of hardware and software. Although, codec 1735 is depicted as a separate component, codec 1735 can be contained within non-volatile memory 1712. By way of illustration, and not limitation, non-volatile memory 1712 can include read only memory (ROM), programmable ROM (PROM), electrically programmable ROM (EPROM), electrically erasable programmable ROM (EEPROM), Flash memory, 3D Flash memory, or resistive memory such as resistive random access memory (RRAM). Non-volatile memory 1712 can employ one or more of the disclosed memory devices, in at least some embodiments. Moreover, non-volatile memory 1712 can be computer memory (e.g., physically integrated with computer 1702 or a mainboard thereof), or removable memory. Examples of suitable removable memory with which disclosed embodiments can be implemented can include a secure digital (SD) card, a compact Flash (CF) card, a universal serial bus (USB) memory stick, or the like. Volatile memory 1710 includes random access memory (RAM), which acts as external cache memory, and can also employ one or more disclosed memory devices in various embodiments. By way of illustration and not limitation, RAM is available in many forms such as static RAM (SRAM), dynamic RAM (DRAM), synchronous DRAM (SDRAM), double data rate SDRAM (DDR SDRAM), and enhanced SDRAM (ESDRAM) and so forth.

Computer 1702 can also include removable/non-removable, volatile/non-volatile computer storage medium. FIG. 17 illustrates, for example, disk storage 1714. Disk storage 1714 includes, but is not limited to, devices like a magnetic disk drive, solid state disk (SSD), flash memory card, or memory stick. In addition, disk storage 1714 can include storage medium separately or in combination with other storage medium including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1714 to the system bus 1708, a removable or non-removable interface is typically used, such as interface 1716. It is appreciated that disk storage 1714 can store information related to a user. Such information might be stored at or provided to a server or to an application running on a user device. In one embodiment, the user can be notified (e.g., by way of output device(s) 1736) of the types of information that are stored to disk storage 1714 or transmitted to the server or application. The user can be provided the opportunity to opt-in or opt-out of having such information collected or shared with the server or application (e.g., by way of input from input device(s) 1728).

It is to be appreciated that FIG. 17 describes software that acts as an intermediary between users and the basic computer resources described in the suitable operating environment 1700. Such software includes an operating system 1718. Operating system 1718, which can be stored on disk storage 1714, acts to control and allocate resources of the computer 1702. Applications 1720 take advantage of the management of resources by operating system 1718 through program modules 1724, and program data 1726, such as the boot/shutdown transaction table and the like, stored either in system memory 1706 or on disk storage 1714. It is to be appreciated that the claimed subject matter can be implemented with various operating systems or combinations of operating systems.

A user enters commands or information into the computer 1702 through input device(s) 1728. Input devices 1728 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1704 through the system bus 1708 via interface port(s) 1730. Interface port(s) 1730 include, for example, a serial port, a parallel port, a game port, and a universal serial bus (USB). Output device(s) 1736 use some of the same type of ports as input device(s) 1728. Thus, for example, a USB port can be used to provide input to computer 1702 and to output information from computer 1702 to an output device 1736. Output adapter 1734 is provided to illustrate that there are some output devices 1736 like monitors, speakers, and printers, among other output devices 1736, which require special adapters. The output adapters 1734 include, by way of illustration and not limitation, video and sound cards that provide a means of connection between the output device 1736 and the system bus 1708. It should be noted that other devices or systems of devices provide both input and output capabilities such as remote computer(s) 1738.

Computer 1702 can operate in a networked environment using logical connections to one or more remote computers, such as remote computer(s) 1738. The remote computer(s) 1738 can be a personal computer, a server, a router, a network PC, a workstation, a microprocessor based appliance, a peer device, a smart phone, a tablet, or other network node, and typically includes many of the elements described relative to computer 1702. For purposes of brevity, only a memory storage device 1740 is illustrated with remote computer(s) 1738. Remote computer(s) 1738 is logically connected to computer 1702 through a network interface 1742 and then connected via communication connection(s) 1744. Network interface 1742 encompasses wire or wireless communication networks such as local-area networks (LAN) and wide-area networks (WAN) and cellular networks. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1744 refers to the hardware/software employed to connect the network interface 1742 to the bus 1708. While communication connection 1744 is shown for illustrative clarity inside computer 1702, it can also be external to computer 1702. The hardware/ software necessary for connection to the network interface 1742 includes, for exemplary purposes only, internal and external technologies such as, modems including regular telephone grade modems, cable modems and DSL modems, ISDN adapters, and wired and wireless Ethernet cards, hubs, and routers.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration and are intended to be non-limiting. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations can be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
    a memory that stores computer executable components; and
    a processor that executes the computer executable components stored in the memory, wherein the computer executable components comprise:
        a collection component that receives patient information for patients currently admitted to a hospital from one or more electronic data sources prior to discharge of the patients, the patient information comprising clinical information about the patients and non-clinical information about the patients, wherein the non-clinical information comprises socioeconomic conditions data, insurance data, behavioral data and mental health data;
        a forecasting component that applies different care outcomes forecasting models to different subsets of parameters extracted from the patient information to predict care outcomes for the patients prior to the discharge of the patients, the care outcomes including discharge times, discharge destinations and their likelihoods, readmission risks and safety risks, wherein the different care outcomes forecasting models comprise machine learning models trained to predict the care outcomes based on learned correlations between the care outcomes and the different subsets of the parameters;
        a reporting component that provides patient care outcomes information to one or more care providers via a graphical user interface displayed at one or more devices to facilitate managing and coordinating inpatient and post-discharge care for the patients, wherein the patient care outcomes information identifies their remaining length of stay, their discharge destinations and likelihoods, their readmission risks, and their safety risks;
        a regulation component that determines whether the discharge destinations predicted for the patients violate one or more defined discharge rules;
        an alert component that generates an alert in response to a determination that a discharge destination violates the one or more defined discharge rules prior to discharge of the patients and provides the alert via the graphical user interface;
        a feedback component that receives feedback information via the graphical user interface regarding patient needs and barriers associated with placing the patients at their discharge destinations; and
        a model optimization component that retrains one or more of the care outcomes forecasting models based on the user feedback to generate updated care outcomes forecasting models with improved accuracy, and wherein the forecasting component further that applies the one or more updated care outcomes forecasting models to at least some of the different subsets of parameters extracted from the patient information to predict updated care outcomes for the patients prior to the discharge of the patients.

2. The system of claim 1, wherein the computer executable components further comprise:
    a display component that displays the patient care outcomes information in real-time at the one or more devices.

3. The system of claim 1, wherein the non-clinical patient information further comprises post-discharge patient support information, including facilities and individuals responsible for caring for the patients after their discharge from the hospital.

4. The system of claim 1, wherein the different care outcomes forecasting models include different discharge destination forecasting models respectively configured to predict intermediate discharge destinations where the patients will be placed after discharge from the hospital based on the different subsets of the parameters, or based on different weighting schemes for the parameters.

5. The system of claim 4, wherein the computer executable components further comprise:
    an optimization component that determines the discharge destinations and their likelihoods based on aggregation of the intermediate discharge destinations, defined discharge constraints, the readmission risks and defined discharge optimization criteria.

6. The system of claim 1, wherein the clinical information comprises temporal clinical data generated over the duration of admittance of the patients at the hospital, wherein the data collection component collects the temporal clinical data over the duration in real-time, and wherein the forecasting component repeatedly applies the outcomes forecasting models to the patient information as new patient information is received.

7. The system of claim 6, wherein the temporal clinical data comprises information regarding treatment units, diagnosis codes, vital signs, laboratory tests, imaging studies, and surgeries.

8. The system of claim 1, wherein the forecasting component further predicts the discharge times based on the discharge destinations and constraints associated with placing the patients at the discharge destinations.

9. The system of claim 1, wherein the computer executable components further comprise:
    a complex patient identification component that identifies complex needs patients included amongst the patients based on the care outcomes predicted for the respective patients, and wherein the reporting component further identifies the complex needs patients with the patient care outcomes information.

10. The system of claim 9, wherein the reporting component further generates a visualization comprising the patient care outcomes information and identifying the complex needs patients and includes the visualization in the graphical user interface.

11. The system of claim 1, wherein the computer executable components further comprise:
a complex patient identification component that identifies complex needs patients included amongst the patients based on the patient information using machine learning and qualitative algorithms, wherein the patient information comprises information regarding patient medical complexity, socioeconomic conditions of the patients, patient insurance, medications taken by the patients, behavioral characteristics of the patients and mental health characteristics of the patients.

12. The system of claim 1, wherein the regulation component further determines whether the discharge times and the discharge destinations predicted for the patients violate the one or more defined discharge rules and wherein the alert component generates the alert in response to a determination that a discharge time and the discharge destination violates the one or more defined discharge rules.

13. A method, comprising:
receiving, by a system comprising a processor, patient information for patients currently admitted to a hospital from one or more electronic data sources prior to discharge of the patients, the patient information comprising clinical information about the patients and non-clinical information about the patients;
applying, by the system, different care outcomes forecasting models to different subsets of parameters extracted from the patient information to predict care outcomes for the patients prior to the discharge of the patients, including discharge times, discharge destinations and their likelihoods, readmission risks and safety risks, wherein the different care outcomes forecasting models comprise machine learning models trained to predict the care outcomes based on learned correlations between the care outcomes and the different subsets of the parameters; and
providing, by the system, care outcomes information identifying the care outcomes predicted for the patients to one or more care providers provides patient care outcomes information to one or more care providers via a graphical user interface displayed at one or more devices to facilitate managing and coordinating inpatient and post-discharge care for the respective patients;
determining, by the system, whether the discharge destinations predicted for the patients violate one or more defined discharge rules;
generating, by the system, an alert in response to a determination that a discharge destination violates the one or more defined discharge rules prior to discharge of the patients;
providing, by the system, the alert via the graphical user interface;
receiving, by the system, feedback information via the graphical user interface regarding patient needs and barriers associated with placing the patients at their discharge destinations; and
retraining, by the system, one or more of the care outcomes forecasting models based on the user feedback to generate updated care outcomes forecasting models with improved accuracy; and
applying, by the system, the one or more updated care outcomes forecasting models to at least some of the different subsets of parameters extracted from the patient information to predict updated care outcomes for the patients prior to the discharge of the patients.

14. The method of claim 13, wherein the non-clinical information comprises patient demographic information, patient insurance information, post-discharge patient support information, patient socioeconomic information, patient mental health information, and patient behavioral information.

15. The method of claim 13, wherein the different care outcomes forecasting models include different discharge forecasting machine learning models respectively configured to predict intermediate discharge destinations where the patients will be placed after discharge from the hospital based on the different subsets of the parameters, or based on different weighting schemes for the parameters.

16. The method of claim 15, further comprising:
predicting, by the system, the discharge destinations and their likelihoods based on aggregation of the intermediate discharge destinations, defined discharge constraints, and defined discharge optimization criteria.

17. The method of claim 13, wherein the clinical information comprises temporal clinical data generated over the duration of admittance of the patients at the hospital, wherein the receiving comprises collecting the temporal clinical data over the duration in real-time, and wherein the applying comprises repeatedly applying the outcomes forecasting models to the patient information as new patient information is received.

18. The method of claim 17, wherein the temporal clinical data comprises information regarding treatment units, diagnosis codes, vital signs, laboratory tests, imaging studies, and surgeries.

19. The method of claim 13, further comprising:
forecasting, by the system, the discharge times based on the discharge destinations predicted for the patients and constraints associated with placing the respective patients at the discharge destinations.

20. The method of claim 13, further comprising:
identifying, by the system, complex needs patients included amongst the patients based on the care outcomes predicted for the respective patients; and
identifying, by the system, the complex needs patients with the patient care outcomes information.

21. The method of claim 20, further comprising:
generating, by the system, a visualization comprising the patient care outcomes information and identifying the complex needs patients; and
displaying, by the system, the visualization via the graphical user interface.

22. The method of claim 13, further comprising:
identifying, by the system, complex needs patients included amongst the patients based on the patient information using machine learning and qualitative algorithms.

23. The method of claim 22, wherein the patient information comprises information regarding patient medical complexity, socioeconomic conditions of the patients, patient insurance, medications taken by the patients, behavioral characteristics of the patients and mental health characteristics of the patients.

24. A non-transitory machine-readable storage medium, comprising executable instructions that, when executed by a processor, facilitate performance of operations, comprising:
receiving patient information for patients currently admitted to a hospital from one or more electronic data sources prior to discharge of the patients, the patient information comprising clinical information about the patients and non-clinical information about the patients;

applying different care outcomes forecasting models to different subsets of parameters extracted from the patient information to predict care outcomes for the patients prior to the discharge of the patients, including discharge times, discharge destinations and their likelihoods, readmission risks and safety risks, wherein the different care outcomes forecasting models comprise machine learning models trained to predict the care outcomes based on learned correlations between the care outcomes and the different subsets of the parameters;

providing care outcomes information identifying the care outcomes predicted for the patients to one or more care providers via a graphical user interface displayed at one or more devices to facilitate managing and coordinating inpatient and post-discharge care for the respective patients;

determining, by the system, whether the discharge destinations predicted for the patients violate one or more defined discharge rules;

generating, by the system, an alert in response to a determination that a discharge destination violates the one or more defined discharge rules prior to discharge of the patients;

providing, by the system, the alert via the graphical user interface;

receiving, by the system, feedback information via the graphical user interface regarding patient needs and barriers associated with placing the patients at their discharge destinations; and retraining, by the system, one or more of the care outcomes forecasting models based on the user feedback to generate updated care outcomes forecasting models with improved accuracy; and applying, by the system, the one or more updated care outcomes forecasting models to at least some of the different subsets of parameters extracted from the patient information to predict updated care outcomes for the patients prior to the discharge of the patients.

25. The non-transitory machine-readable storage medium of claim 24, wherein the non-clinical information comprises patient demographic information, patient insurance information, post-discharge patient support information, patient socioeconomic information, patient mental health information, and patient behavioral information.

26. The non-transitory machine-readable storage medium of claim 24, wherein the different care outcomes forecasting models include different discharge forecasting machine learning models respectively configured to predict intermediate discharge destinations where the patients will be placed after discharge from the hospital based on the different subsets of the parameters or based on different weighting schemes for the parameters.

27. The non-transitory machine-readable storage medium of claim 26, wherein the operations further comprise:
predicting the discharge destinations and their likelihoods based on aggregation of the intermediate discharge destinations, defined discharge constraints, and defined discharge optimization criteria.

28. The non-transitory machine-readable storage medium of claim 24, wherein the clinical information comprises temporal clinical data generated over the duration of admittance of the patients at the hospital, wherein the receiving comprises collecting the temporal clinical data over the duration in real-time, and wherein the applying comprises repeatedly applying the outcomes forecasting models to the patient information as new patient information is received.

29. The non-transitory machine-readable storage medium of claim 27, wherein the temporal clinical data comprises information regarding treatment units, diagnosis codes, vital signs, laboratory tests, imaging studies, and surgeries.

* * * * *